US011099170B2

(12) United States Patent
Leburton

(10) Patent No.: US 11,099,170 B2
(45) Date of Patent: Aug. 24, 2021

(54) PARALLEL DNA DETECTION BY SOLID-STATE MULTI-PORE SYSTEMS AND ASSOCIATED METHODS

(71) Applicant: THE BOARD OF TRUSTEES OF THE UNIVERSITY OF ILLINOIS, Urbana, IL (US)

(72) Inventor: Jean-Pierre Leburton, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 25 days.

(21) Appl. No.: 16/439,524

(22) Filed: Jun. 12, 2019

(65) Prior Publication Data
US 2019/0383789 A1    Dec. 19, 2019

Related U.S. Application Data

(60) Provisional application No. 62/684,378, filed on Jun. 13, 2018.

(51) Int. Cl.
*G01N 33/487*    (2006.01)
*G01N 27/447*    (2006.01)
(Continued)

(52) U.S. Cl.
CPC .    *G01N 33/48721* (2013.01); *G01N 27/44791* (2013.01); *H01L 29/1606* (2013.01); *H01L 29/24* (2013.01)

(58) Field of Classification Search
None
See application file for complete search history.

(56) References Cited

U.S. PATENT DOCUMENTS 8,702,929 B2    4/2014    Leburton et al.
10,345,289 B2    7/2019    Leburton
(Continued)

OTHER PUBLICATIONS

Gadaleta, A. et al., "Sub-additive ionic transport across arrays of solid-state nanopores", Sub-additive ionic transport across arrays of solid-state nanopores; Phys. Fluids 26, 012005 (2014); https://doi.org/10.1063/1.4863206 Submitted: Sep. 21, 2013. Accepted: Jan. 11, 2014. Published Online: Jan. 31, 2014.
(Continued)

*Primary Examiner* — J. Christopher Ball
(74) *Attorney, Agent, or Firm* — Guntin & Gust, PLC; Matthew Tropper

(57) ABSTRACT

Aspects of the subject disclosure may include, for example, an apparatus comprising: a dielectric substrate; a plurality of membranes positioned upon the dielectric substrate, wherein each of the plurality of membranes has a first side and a second side, wherein each of the plurality of membranes has a pore disposed therein, wherein each pore extends through each respective membrane from the first side of the respective membrane to the second side of the respective membrane, wherein each pore is associated with a corresponding hole that extends through the dielectric substrate, and wherein each of the plurality of membranes is not in direct contact with any other of the plurality of membranes; and a plurality of electrode pairs, wherein each of the plurality of electrode pairs is in contact with a single respective one of the plurality of membranes. Additional embodiments are disclosed.

23 Claims, 18 Drawing Sheets

(51) Int. Cl.
*H01L 29/16* (2006.01)
*H01L 29/24* (2006.01)

(56) References Cited

U.S. PATENT DOCUMENTS

| | | | |
|---|---|---|---|
| 10,677,752 B2 | 6/2020 | Leburton | |
| 2014/0079936 A1* | 3/2014 | Russo | B81C 1/00087 |
| | | | 428/220 |
| 2014/0174927 A1 | 6/2014 | Bashir et al. | |
| 2015/0259724 A1 | 9/2015 | Guan et al. | |
| 2015/0377830 A1 | 12/2015 | Baldauf et al. | |
| 2016/0054260 A1 | 2/2016 | Leburton | |
| 2016/0187290 A1 | 6/2016 | Leburton | |
| 2018/0088104 A1 | 3/2018 | Aksimentiev et al. | |
| 2019/0383789 A1 | 12/2019 | Leburton | |
| 2020/0333290 A1 | 10/2020 | Leburton et al. | |

OTHER PUBLICATIONS

Pud, Sergii et al., "Mechanical Trapping of DNA in a Double-Nanopore System", DOI: 10.1021/acs.nanolett.6b04642 Nano Lett. 2016, 16, 8021-8028.

Athreya, et al., "Large Scale Parallel DNA Detection by 2D Solid-State Multi-Pore Systems", Biophysical Society meeting on Feb. 17, 2018, Feb. 17, 2018, 1pg.

Athreya, et al., "Large Scale Parallel DNA Detection by Two-Dimensional Solid-State Multipore Systems", ACS Sensors; Apr. 17, 2018, 3, 1032-1039 (Supporting Information), Apr. 17, 2018, 8 pgs.

Athreya, N. B. M. et al., Large Scale Parallel DNA Detection by Two-Dimensional Solid-State Multipore Systems; ACS Sensors; Apr. 17, 2018, 3, 1032-1039, Apr. 17, 2018, 8 pgs.

Avdoshenko, S.M. et al., "Dynamic and Electronic Transport Properties of DNA Translocation through Graphene Nanopores", Nano Lett. 2013, 13, 1969-1976.,Apr. 15, 2013.

Bezrukov, S. et al., "Probing alamethicin channels with water-soluble polymers Effect on conductance of channel states", Biophys. J. 1993, 64,16-25, Jan. 1, 1993, 10pgs.

Branton, Daniel et al., "The Potential and Challenges of Nanopore Sequencing", Nature Biotechnology, vol. 26, No. 10, pp. 1146-1153, 2008, 8 pages.

Carson, Spencer et al., "Challenges in DNA Motion Control and Sequence Readout Using Nanopore Devices", Department of Physics, Northeastern University, Nanotechnology 26 (2015) 074004 (14pp), Feb. 2, 2015, pp. 1-14.

Cohen-Tanugi, D. et al., "Water Desalination across Nanoporous Graphene", Nano Lett. 2012, 12, 3602-3608, 2012, 7.

Dekker, C., "Solid-State Nanopores", Nat. Nanotechnol. 2007, 2, 209-215., Apr. 1, 2007, 209-215.

Dimitrov, V. et al., "Nanopores in solid-state membranes engineered for single molecule detection", Nanotechnology 2010, 21, 065502, Jan. 11, 2010, 12 pgs.

Essmann, U. et al., a smooth particle mesh Ewald method. J. Chem. Phys. 1995, 103, 8577-8593., 1995, 18 pgs.

Feller, S.E., Constant pressure molecular dynamics simulation: the Langevin piston method. J. Chem. Phys. 1995, 103, 4613-4621., 1995, 10pgs.

Feng, et al., "Nanopore-based Fourth-generation DNA Sequencing Technology", Genomics, Proteomics Bioinf. 2015, 13, p. 4-16., 2015, 13 pgs.

Feng, et al., "Single-Layer MoS2 Nanopores as Nanopower Generators", Nature 2016, 197-200., 2016.

Garaj, S. et al., "Graphene as a subnanometre trans-electrode membrane", Nature 2010, 467, 190-193, Sep. 9, 2010.

Girdhar, A. et al., Graphene quantum point contact transistor for DNA sensing. Proc. Natl. Acad. Sci. U. S. A. 2013, 110, 16748-16753, Oct. 15, 2013, 6 pgs.

Girdhar, A. et al., "Tunable graphene quantum point contact transistor for DNA detection and characterization", Nanotechnology 2015, 26, 134005, Mar. 13, 2015, 11 pgs.

Gracheva, M.E. et al., Electrical signatures of single-stranded DNA with single base mutations in a nanopore capacitor. Nanotechnology 2006, 17, 3160-3165, 2006.

Gracheva, M.E. et al., "Simulation of the Electric Response of DNA 493 Translocation through a Semiconductor Nanopore-capacitor", Nano-technology 2006, 17, 622-633, 2006, 622-633.

Hall, James E., "Access Resistance of a Small Circular Pore", Department of Physiology and Pharmacology, Drake University Medical Center, The Journal of General Physiology, vol. 66, Jun. 6, 1975, pp. 531-532.

Haque, et al., "Solid-state and biological nanopore for real-time sensing of single chemical and sequencing of DNA", NanoToday, vol. 8, Issue 1, Feb. 2013, pp. 56-74, Feb. 4, 2013, 19.

Heerema, S.J. et al., Probing DNA translocations with inplane current signals in a graphene nanoribbon with a nanopore. ACS Nano, Feb. 23, 2018, 12, 2623-2633., Feb. 23, 2018, 11 pgs.

Humphrey, W. et al., VMD: visual molecular dynamics. J. Mol. Graphics 1996, 14, 33-38, 1996, 6 pgs.

Hyun, C. et al., "Probing Access Resistance of Solid-State Nanopores with a Scanning-Probe Microscope Tip", Small 2012, 8, 385-392, 2012.

Jorgensen, W. L., Comparison of simple potential functions for simulating liquid water. J. Chem. Phys. 1983, 79, 926-935., 1983, 11 pgs.

Kowalczyk, Stefan W. et al., "Modeling the Conductance and DNA Blockade of Solid-State Nanopores", Nanotechnology 22, Jul. 6, 2011, 6 pages.

Krapf, D, "Fabrication and Characterization of Nanopore-Based Electrodes with Radii down to 2 Nm", Nano Lett. 2006, 6, 105-109., 2006, 5pgs.

Li, et al., "Ion-Beam Sculpting at Nanometre Length Scales", Nature 2001, 166-169, Jul. 12, 2001, 166-169.

Mackerell, A. D. et al., "All-Atom Empirical Potential for Molecular Modeling and Dynamics Studies of Proteins", Journal Phys. Chem B, 1998, 3586-3616.

Merchant, C. A. et al., "DNA Translocation through Graphene Nanopores", Nano Lett. 2010, 547 10, 2915-2921, Jul. 23, 2010, 7.

Phillips, James C., "Scalable Molecular Dynamics with NAMD", Journal of Computer Chemistry, Wiley Periodicals, 2005, 1781-1802.

Postma, Henk W., Rapid sequencing of individual DNA molecules in graphene nanogaps. Nano letters 10.2 (2010): 420-425, Jan. 4, 2010.

Prasongkit, J et al., "Transverse Conductance of DNA Nucleotides in a Graphene Nanogap from First Principles", Nano Lett. 2011, 11, 1941-1945, Apr. 15, 2011.

Pud, Sergii et al., "Mechanical Trapping of DNA in a Double-Nanopore System", DOI: 10.1021/acs.nanolett.6b04642 Nano Lett. 2016, 16, pp. 8021-8028 (including a Supporting Information document) Nov. 28, 2016, Nov. 28, 2016, 34 pgs.

Rhee, M. et al., "Nanopore Sequencing Technology: Research Trends and Applications", Trends in Biotechnology. 2006, 24, 580-586., 2006, 7.

Saha, K. et al., "DNA Base-Specific Modulation of Microampere Transverse Edge Currents through a Metallic Graphene Nanoribbon with a Nanopore", Nano Lett. 2012, 12, 571 50-55., Dec. 5, 2011, 6 pgs.

Sarathy, A. et al., Graphene nanopores for electronic recognition of DNA methylation. J. Phys. Chem. B, Dec. 30, 2016, 121, 3757-3763, Dec. 30, 2016, 7.

Schneider, G. et al., "DNA Translocation through Graphene Nanopores", Nano Letters, 2010, Kavli Institute of Nanoscience, Lorentzweg 1, 2628 CJ Delft, The Netherlands, Jul. 7, 2010, 5.

Siwy, Z. et al., "Fabrication of a Synthetic Nanopore Ion Pump", Phys. Rev. Lett. 2002, 89, 198103, Oct. 18, 2002, 4pgs.

Storm, A. J. et al., "Fabrication of solid-state nanopores with single-nanometre precision", Precision. Nat. Mater. 2003, 2, 537-540., Jul. 13, 2003, 5.

Surwade, et al., "Water desalination using nanoporous single-layer graphene", Natural Nanotechnology. 2015, 10, 459-524., 2015.

Traversi, F. et al., "Detecting the translocation of DNA through a nanopore using graphene nanoribbons", Nat. Nanotechnol. 2013, 8, 939-945., Nov. 17, 2013, 7.

(56) References Cited

OTHER PUBLICATIONS

Van Dijk, M., 3D-Dart: a DNA structure modelling server. Nucleic Acids Research 2009, 37, W235-W239., Apr. 14, 2009, 5.
Venkatesan, et al., "Nanopore sensors for nucleic acid analysis", Natural Nanotechnology, 2011, 6, 615-624., 2011.
Venta, et al., ". Differentiation of Short, Single-Stranded DNA Homopolymers in Solid-State Nanopores", ACS Nano, 2013, 7 (5), pp. 4629-4636., Apr. 26, 2013, 8.
Wang, J. et al., "Effects of access resistance on the resistive-pulse caused by translocating of a nanoparticle through a nanopore", RSC Adv. 2014, 4, 7601-7610, Jan. 7, 2014, 10pgs.
Xie, P. et al., "Local electrical potential detection of DNA by nanowire-nanopore sensors", Nat. Nanotechnol. 2012, 7, 119-125, Feb. 1, 2012, 7.

\* cited by examiner

Sensing, by a processing system including a processor, a first characteristic associated with a first translocation of a first biomolecule through a first pore of a first membrane of a plurality of membranes, wherein the first membrane is disposed on a dielectric substrate, wherein the first pore goes through the first membrane, wherein the first pore is associated with a corresponding first hole that extends through the dielectric substrate, and wherein the first membrane is in electrical contact with a first pair of electrodes via which the first characteristic is sensed
1202

Sensing, by the processing system, a second characteristic associated with a second translocation of a second biomolecule through a second pore of a second membrane of the plurality of membranes, wherein the second membrane is disposed on the dielectric substrate, wherein the second pore goes through the second membrane, wherein the second pore is associated with a corresponding second hole that extends through the dielectric substrate, wherein the second membrane is not in direct contact with the first membrane, wherein the second membrane is not in electrical contact with the first pair of electrodes, and wherein the second membrane is in electrical contact with a second pair of electrodes via which the second characteristic is sensed
1204

Obtaining a first electrical characteristic associated with a first translocation of a first biomolecule through a first pore of a first membrane of a plurality of membranes, wherein the first membrane is located on a dielectric substrate, wherein the first pore goes through the first membrane, wherein the first pore is associated with a corresponding first hole that extends through the dielectric substrate, and wherein the first membrane is in electrical contact with a first pair of electrodes via which the first electrical characteristic is sensed

1302

Obtaining a second electrical characteristic associated with a second translocation of a second biomolecule through a second pore of a second membrane of the plurality of membranes, wherein the second membrane is located on the dielectric substrate, wherein the second pore goes through the second membrane, wherein the second pore is associated with a corresponding second hole that extends through the dielectric substrate, wherein the second membrane is not in direct contact with the first membrane, wherein the second membrane is not in electrical contact with the first pair of electrodes, and wherein the second membrane is in electrical contact with a second pair of electrodes via which the second electrical characteristic is sensed

PARALLEL DNA DETECTION BY SOLID-STATE MULTI-PORE SYSTEMS AND ASSOCIATED METHODS

CROSS-REFERENCE TO RELATED APPLICATION(S)

The present application claims the benefit of priority to U.S. Provisional Patent Application No. 62/684,378, filed on Jun. 13, 2018, the disclosure of which is incorporated by reference herein in its entirety.

FIELD OF THE DISCLOSURE

The subject disclosure relates generally to parallel DNA detection by solid-state multi-pore systems and associated methods. In one specific example, the parallel DNA detection can utilize a 2D solid-state multi-pore system.

BACKGROUND

In the recent past, solid-state nanopores (see generally references 1-6) have attracted significant attention for their potential biomedical applications in the fields of single-molecule detection (see generally references 7,8), osmotic power generation (see generally reference 9), and water desalination (see generally references 10,11). Such solid-state nanopores offer a multitude of advantages over biological nanopores for DNA sensing, and possibly sequencing, by overcoming detection bottlenecks such as constant pore size, and/or limited chemical, thermal and mechanical stability that are inherently present (see generally references 3,12). However, such solid-state nanopores typically still have shortcomings such as significant thermal conformational DNA fluctuations, very fast translocation rate, and/or undesirable interaction of DNA with the solid-state membranes, which typically hinder the realization of a successful genome sequencing device (see generally references 13-15).

Among the wide range of practical solid-state materials investigated for nanopore sequencing technology, two-dimensional (2D) atomically thin layered materials such as graphene or transition metal dichalcogenide (TMD) monolayers are of particular interest due their ability to detect individual DNA nucleotides. In this context, detection of a DNA molecule translocating through a graphene nanopore by monitoring the variations of the ionic blockade current are already reported by several groups (see generally references 16-18).

Apart from their high stability, cost-effectiveness, robustness, ability to adjust surface properties, and controllability in designing pore shape and pore size, solid-state nanopores offer a vital advantage of multiplexing, which is of paramount importance toward the realization of sensors for rapid detection of biomolecules such as nucleic acids and proteins. Hence, in the context of osmotic-power generation, Gadaleta et al. experimentally reported scaling of ion conductance across an array of nanopores (see generally reference 19). Additionally, a double nanopore setup has been reported by Pud et al., where a very long dsDNA strand is mechanically trapped to increase the dwelling time within the nanopores (see generally reference 20). However, both the above-mentioned studies do not account for the simultaneous detection of multiple DNA strands in a multipore system.

BRIEF DESCRIPTION OF THE DRAWINGS

Reference will now be made to the accompanying drawings, which are not necessarily drawn to scale, and wherein:

FIG. 1A shows a plot of per-pore ionic conductance as a function of number of pores (N), for varying separation distances (L), with each nanopore diameter being 2.6 nm (FIG. 1B shows a schematic drawing of a plurality of nanopores separated by distance L). Further, FIG. 1C shows a plot of the ionic conductance blockade (described in Equation 3 (below)) as a function of the number of nanopores (N). Further still, FIG. 1D shows a schematic drawing of an array of pores placed on a dielectric showing an experimental setup for measuring the total ionic conductance of the whole system ($G_{open}$) and the per-pore conductance ($G_{pore}$).

FIG. 2A shows ionic current traces measured across each nanopore ("pore-1" and "pore-2"—shown in the lower two traces). The sum of the two individual currents ("pore-1+pore-2"— shown in the generally topmost trace) is equal to the current calculated for the whole system ("total"—shown in the trace generally just below the "pore-1+pore-2" trace). Further, FIG. 2B shows a schematic drawing of an open-pore MD model, where two 9 nm×9 nm graphene sheets 211,212 with a 2.6 nm diameter nanopore placed on a 5 nm $Si_3N_4$ dielectric 213 (with respective holes at locations corresponding to the nanopores) is immersed in a 1 M KCl solution. Further still.

FIG. 3A shows a molecular dynamics simulation setup of 25 bp dsDNA (double stranded DNA) translocating through a graphene membrane 311 with 2.6 nm diameter pore. Further, FIG. 3B shows a top view of the graphene QPC (quantum point contact) with a 2.6 nm nanopore diameter and the width of the constriction (Wreck) set to 1.2 nm.

FIG. 4A shows time traces of ionic current (the total ionic current is shown as the lighter, "background" trace; the average ionic current is shown as the generally bottom of the two darker traces) and transverse sheet current (shown as the generally top of the two darker traces) obtained for a trajectory obtained from MD simulations. Further, FIG. 4B shows current signals obtained for another trajectory of DNA translocating in the same system (again, the total ionic current is shown as the lighter, "background" trace; the average ionic current is shown as the generally bottom of the two darker traces; and transverse sheet current is shown as the generally top of the two darker traces).

FIG. 5A shows three sequences of conformations of dsDNA during translocation events through the multipore system (there are three sequences—one case shown in column "i"; a second case shown in column "ii", and a third case shown in column "iii"). Each respective event corresponds to the dip in the current signal for the three respective cases (see FIG. 5B). Further, FIG. 5B shows ionic currents in the three panels along the top row corresponding to the three different cases (see "i", "ii", "iii" in FIG. 5A) of simultaneous translocation of two dsDNA through the multipore system (in each of the three panels of the top row of FIG. 5B, the total ionic current is shown as the lighter, "background" trace, and the average ionic current is shown as the darker trace). As seen, case "i" is when both dsDNA translocate together in two nanopores, case "ii" is when a dsDNA translocation through one of nanopore occurs with a time offset resulting in an overlap between the events on time scale, and case "iii" is when a dsDNA completes translocation through one nanopore and is followed by a translocation through the other nanopore. Further, still referring to FIG. 5B, this shows in the three panels along the bottom row transverse sheet currents obtained from the two graphene membranes (labeled here as "Membrane-1" and "Membrane-2") for the corresponding three cases of ionic currents shown in the top row of panels in FIG. 5B.

FIG. 6 shows ionic currents in the three panels along the top row corresponding to the three different cases (see "i", "ii", "iii" in FIG. 5A) of simultaneous translocation of two dsDNA through a different sized multipore system (in each of the three panels of the top row of FIG. 6, the total ionic current is shown as the lighter, "background" trace, and the average ionic current is shown as the darker trace). Further, this FIG. 6 shows in the three panels along the bottom row transverse sheet currents obtained from the two graphene membranes (labeled here as "Membrane-1" and "Membrane-2", but different from the membranes referred to in FIGS. 5A, 5B) for the corresponding three cases of ionic currents shown in the top row of panels of FIG. 6.

FIG. 8A shows a schematic illustration of an open-pore MD model with 2.6 nm and 3.6 nm diameter nanopores. The nanopores go through graphene membranes 811, 812 and are aligned with corresponding holes in dielectric 813 (in this example, $Si_3N_4$). Further, FIG. 8B shows ionic current traces measured across each nanopore ("pore-1" and "pore-2"). The sum of the two individual currents calculated by creating a virtual box for each nanopore membrane ("pore-1+pore-2") is equal to the total current calculated for the whole system if one set of electrodes were used for obtaining the ionic current signal (see the trace labelled "total"). Further still, the inset Table shows the total number of ions in each virtual box (created around the nanopore membranes) at 0 ns and 5 ns.

FIG. 11A shows ionic and transverse sheet current obtained for a DNA translocating through a 3.6 nm diameter pore trajectory obtained from MD simulations and electronic transport calculations respectively. Further, FIG. 11B shows a top view of the graphene QPC with a 3.6 nm nanopore diameter and the width of the constriction ($W_{neck}$) set to 1.2 nm, which is the same used for 2.6 nm diameter pore.

FIG. 12 depicts an illustrative embodiment of a method in accordance with various aspects described herein.

FIG. 13 depicts an illustrative embodiment of a method in accordance with various aspects described herein.

DETAILED DESCRIPTION

Figure 1A:
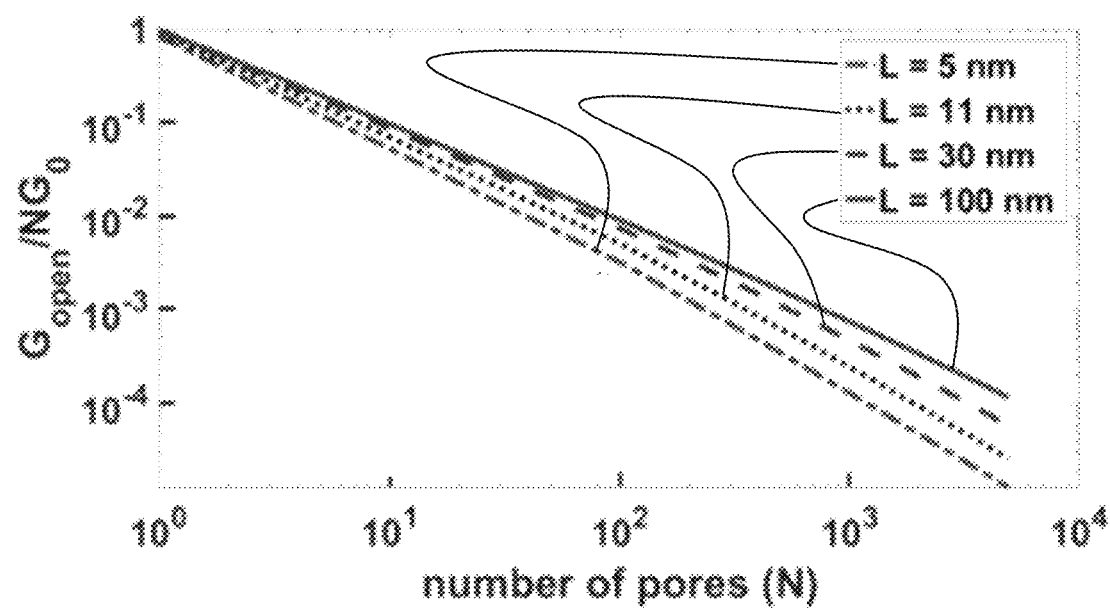
FIGS. 1A, 1B, 1C and 1D relate to conventional aspects of scaling the nanopore density and effect on ionic conductance. More particularly.
Figure 1B:
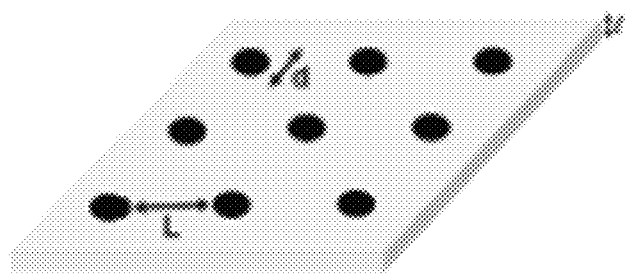

Reference will now be made to an overview of various embodiments. In order to overcome one or more shortcomings of certain conventional parallel DNA detection using ionic blockade, various embodiments provides a novel device comprising of an array of nanopore membranes (e.g., 2D nanopore membranes) for detecting several biomolecules based on the variation of the transverse sheet current across each membrane. Various embodiments leverage the advantage of multiplexing by exploring the operation of a double-pore system by means of all-atom molecular dynamics (MD) simulations coupled with electronic transport calculations (see generally reference 25). First, from the analysis of the behavior of ion flow in an open-pore system, the double-pore system is modelled as a parallel-resistor circuit to investigate the ionic and transverse sheet currents for three cases of parallel DNA translocation through the double-pores. The system of this example consists of a single set of electrodes to drive the DNAs from cis- to trans-membrane and corresponding electrodes per individual pore membrane to sense the transverse sheet currents. It is then shown that inhomogeneities in pore dimension across an array of nanopores do not impede the simultaneous sensing of DNA, because of the remarkable conductive tunability of each graphene nanopore membrane by the gate voltage to achieve high detection sensitivity (see generally reference 25).

In summary, one embodiment shows a design of a massively parallel biomolecular detection platform of solid state nanopores. The sensing membranes can comprise electrically active two-dimensional materials allowing for simultaneous multi-channel measurements of the translocating DNA via ionic and transverse currents. The open-pore behavior of a solid-state multi-pore detection platform according to an embodiment shows that such a system can be modeled as a parallel resistors model with contributions from the pore and access resistance contributions from the different pores. To illustrate the operation of a multi-pore system (according to an embodiment), three cases of ionic and transverse sheet currents for the respective possible arrangements of multiple DNA translocating in different nanopores are discussed. The transverse sheet currents, obtained for each of the individual nanopore membranes, is anticipated to be the crucial factor in realizing a massive array (e.g., 2D array) of solid-state nanopores for parallel biomolecule detection. In addition, the same analysis on a different sized multi-pore system showed similar behavior, illustrating the generalization of the design to arbitrarily sized and shaped pores on different sensing membranes, which allows easy integration into semiconductor electronics. It is believed that the methodology presented herein, that can be extended to one or more 2D TMD nanopore membranes, is a step closer towards realizing an innovative sensor for rapid detection of biomolecules, possibly even genome sequencing. These devices hold the potential for utilization in the risk assessment of early diagnosis as well as for seamless integration with semiconductor electronics.

Figure 7:
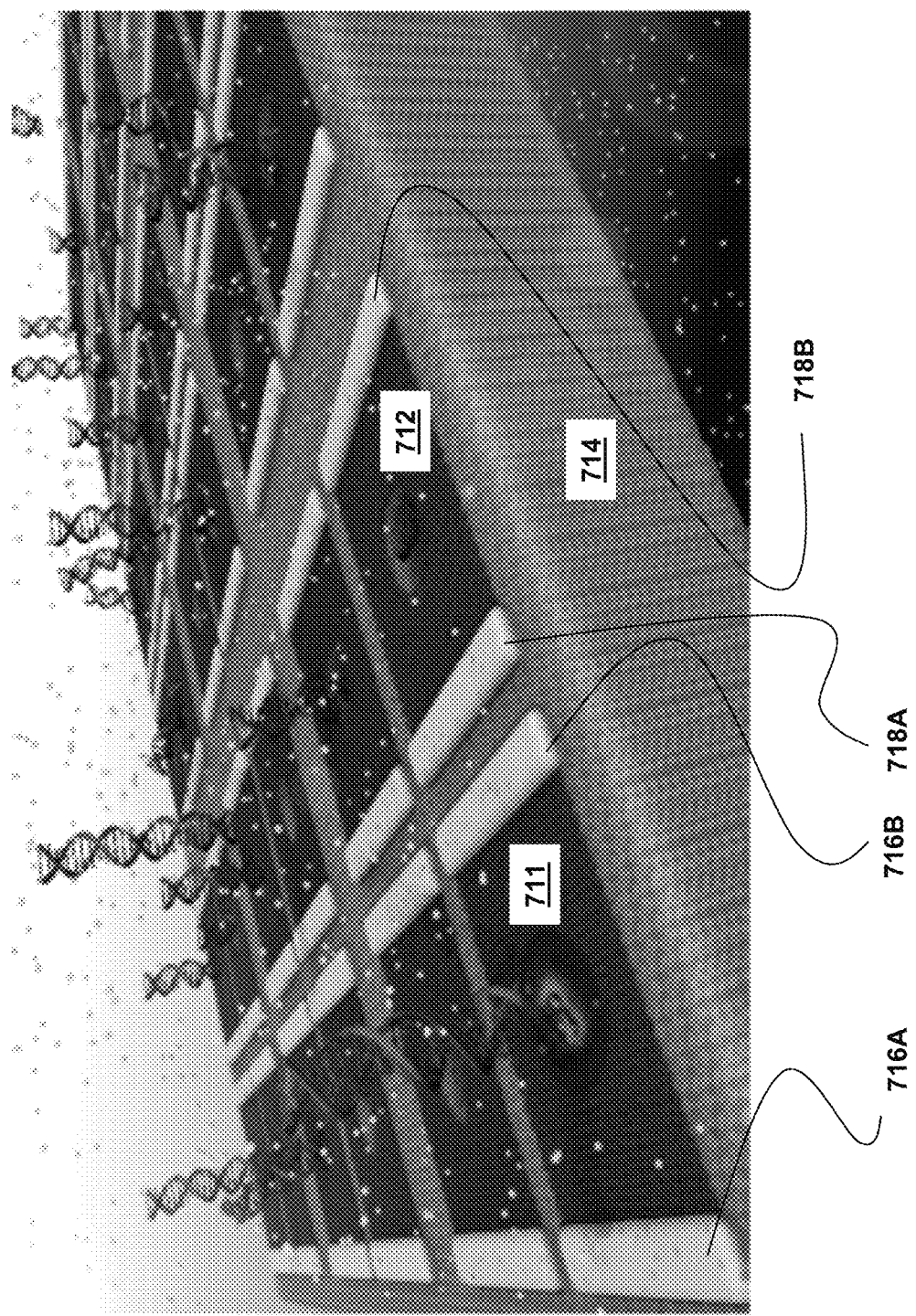
FIG. 7 relates to a schematic representation, according to an embodiment, of a massively parallel arrangement of an array of 2D nanopore membranes (two of which have been labelled as 711, 712) grown on a dielectric substrate 714 (this arrangement provides concurrent detection of multiple DNAs through a multi-pore system using sheet currents). Also labelled in this FIG. are two sets of electrodes—716A, 716B and 718A,718B.

Referring now to FIG. 7, this shows a schematic representation of a massively parallel arrangement (according to an embodiment) of an array of 2D nanopore membranes grown on a dielectric substrate. Each graphene membrane (two of which are labelled—711,712) is connected to a source and drain electrode (two pairs of which are labelled—716A,716B and 718A,718B). The transverse sheet current across each membrane is measured by a respective pair of electrodes. The entire setup is submerged in an ionic solution containing multiple dsDNA strands. A voltage applied across the whole system forces the dsDNA strands to translocate through the nanopores. This FIG. 7 shows multiple events of DNA translocations through each of the nanopores. The potential induced by a dsDNA around the pore of the corresponding g-QPC while translocating through the nanopore is also represented. As opposed to ionic current measurements, whereby individual flow cells are required for each DNA translocation, this transverse sheet current device arrangement is obtained for each of the individual nanopores within a single flow cell, illustrating the concept of concurrent detection of multiple DNAs through a multi-pore system using sheet currents.

Figure 1C:
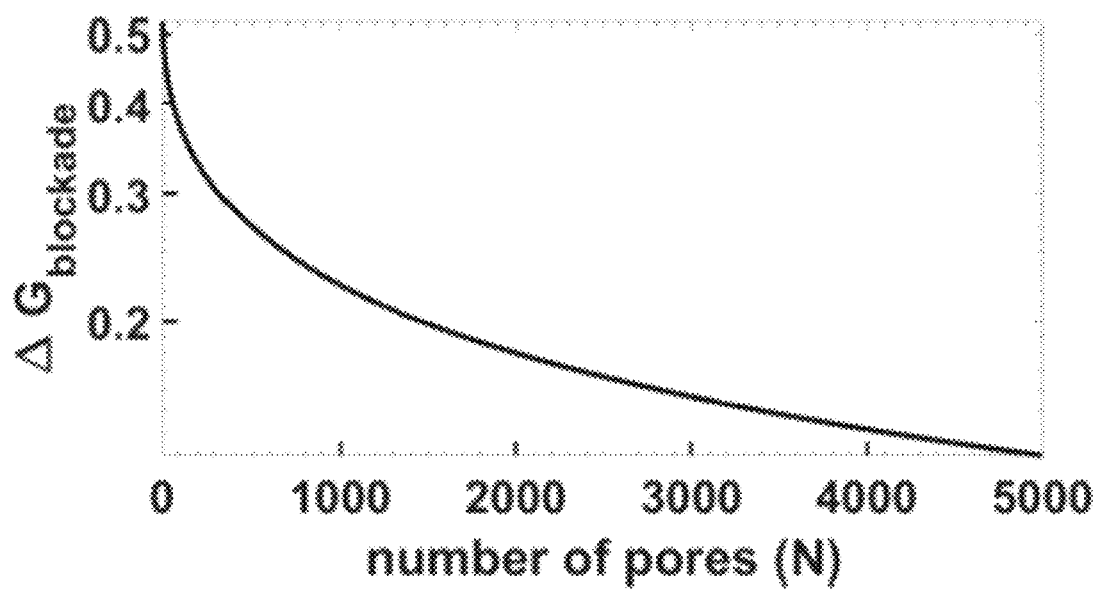
Figure 1D:
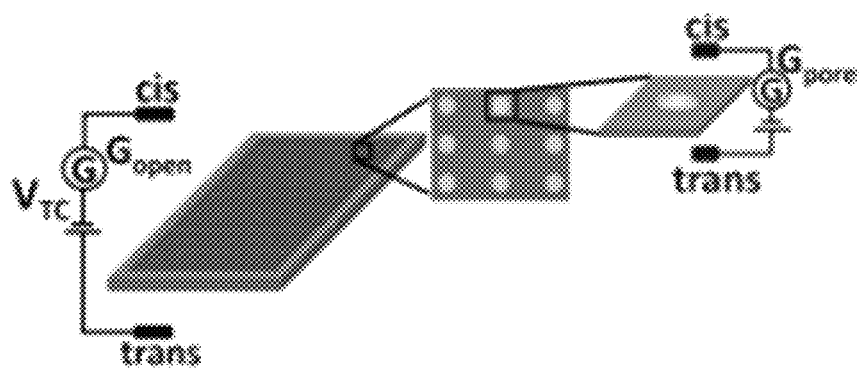

Reference will now be made to certain aspects of per pore conductance. It is known that the conductance per-pore ($G_{pore}$) for a system consisting of a few isolated circular nanopores can be written as (21)

$$G_{pore} = \frac{G_{open}}{N} = \sigma\left[\frac{4l}{\pi d^2} + \frac{1}{d}\right]^{-1} \quad (1)$$

where $G_{open}$ is the cumulative open-pore conductance due to N nanopores characterized by a length (l) and diameter (d), immersed in an ionic solution with a bulk conductivity $\sigma$. In massively parallel nanopore based sensing devices using biological pores such as the PromethION from Oxford Nanopore Technologies, close to 3000 individual pores are utilized. However, when a similar setup is mimicked using solid state nanopores, it has been shown that as the number of nanopores increases, the per-pore conductance strongly decreases (see generally reference 19). This is due to the dominant access effects at the entrance of the pore compared to the bulk effect arising from inside the pore. Therefore, the effective open pore conductance due to many identical pores arranged on a two-dimensional grid can be modeled as (see generally reference 19)

$$G_{pore} = \sigma\left[\frac{4l}{\pi d^2} + \frac{1}{d} + \gamma_N \frac{d}{2L}\right]^{-1} \quad (2)$$

where, $\gamma N$ is the geometric factor accounting for the 2D compact arrangement of N-nanopores. For large N, $\gamma N$ is shown to be $N^{1/2}$. Consequently, the effective conductance blockade per nanopore due to DNA translocation reads $$\Delta G = \frac{G_{open} - G_{blocked}}{G_{open}} \quad (3)$$

where $G_{blocked}$ is the ionic conductance due to the translocation of DNA through the pore, which is calculated by Equation 2 (above) where d is replaced by $$d_{eff} = \sqrt{d_{pore}^2 - d_{DNA}^2},$$

with $d_{DNA}$ (diameter of the dsDNA molecule) taken to be 2.2 nm. FIG. 1A displays the total ionic conductance normalized by the number of nanopores, where it is seen that the cumulative open-pore conductance drastically reduces as the density of nanopores on the chip increases. Subsequently, the corresponding conductance blockade per nanopore due to DNA translocation also drastically reduces as shown in FIG. 1C. In fact, one can easily estimate that the per-pore conductance blockade in a huge array consisting of 2.6 nm diameter pores is equivalent to the conductance blockade obtained by a DNA translocating though a single isolated nanopore characterized by a significantly larger diameter.

Owing to the conductive properties of graphene nanoribbons, theoretical studies have put forward the possibility of monitoring resistive modulations in electronic transverse currents along the membrane to detect DNA translocations through nanopores (see generally references 22-25). Subsequent experimental studies have confirmed this conjecture directly by demonstrating the detection of DNA by electronic transverse current measurements (see generally references 26-28).

Reference will now be made to certain results according to various embodiments. Investigated first is an open-pore model via ionic current calculations to understand the behavior of ionic flow through a double pore. For this investigation, considered were two monolayer graphene membranes each measuring 9 nm×9 nm with a 2.6 nm diameter circular pore drilled in the center. Graphene membranes were separated by 2 nm, housed on a 5-nm-thick Silicon nitride ($Si_3N_4$) and submerged in a 1.0 M KCl solution (see FIG. 2B). For the MD simulations, constraints were set such that the ions are prevented from flowing through the gap between the two membranes. Experimentally, this would be inherently achieved by insulating the graphene membranes from one another with a dielectric material such as Silicon dioxide ($SiO_2$) or Aluminum oxide ($Al_2O_3$) so that the flow of ions is restricted to the nanopores.

Figure 2A:
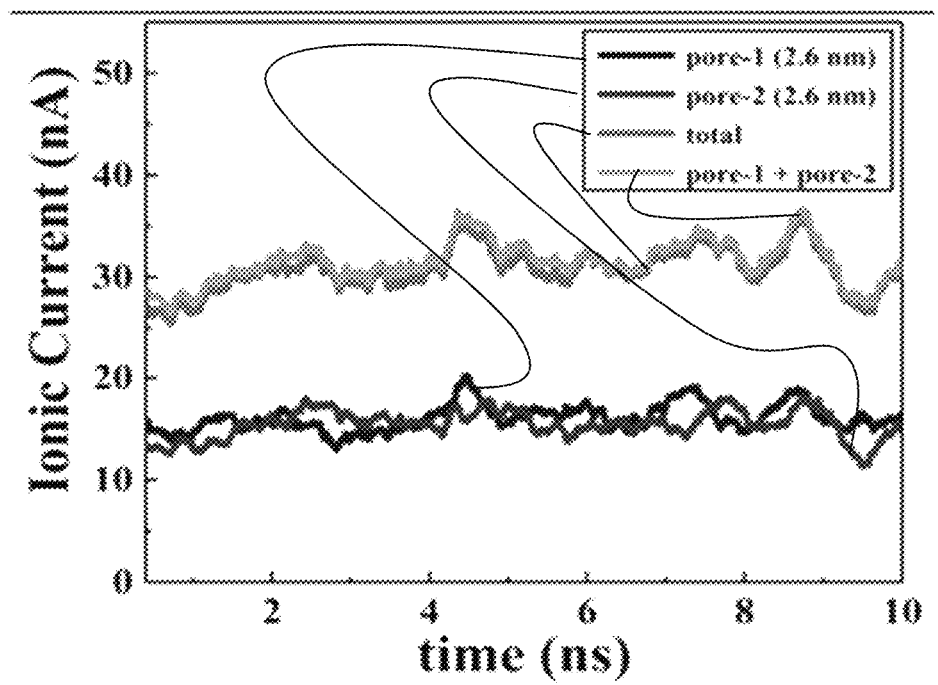
FIGS. 2A and 2B relate to characterization of a multipore system according to an embodiment. More particularly
Figure 2B:
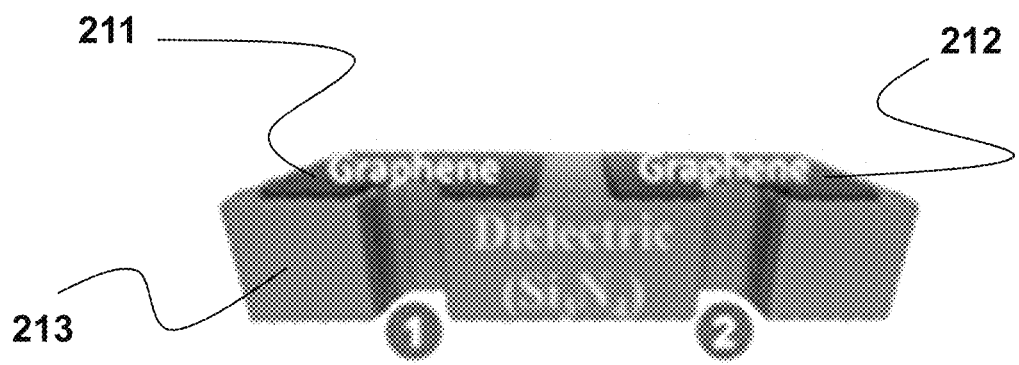

The ionic currents are calculated (see Equation 1 (above) in each of the pores individually by creating a virtual box in the x-y plane matching that of the graphene membrane area with the z-direction being perpendicular to the pore. The resulting ionic currents through pore-1 (see FIG. 2B) and pore-2 (see FIG. 2B) are found to be of similar magnitudes as shown in FIG. 2A. Also, the sum of ionic current (see the topmost trace in FIG. 2A) through each pore is found to be equal to the total ionic current of the whole system (see the trace directly below the topmost trace in FIG. 2A), calculated for the entire system consisting of both graphene membranes. Therefore, one can conclude that the ionic current in the double-pore system can be characterized as a sum of contributions of individual nanopores.

Figure 8A:
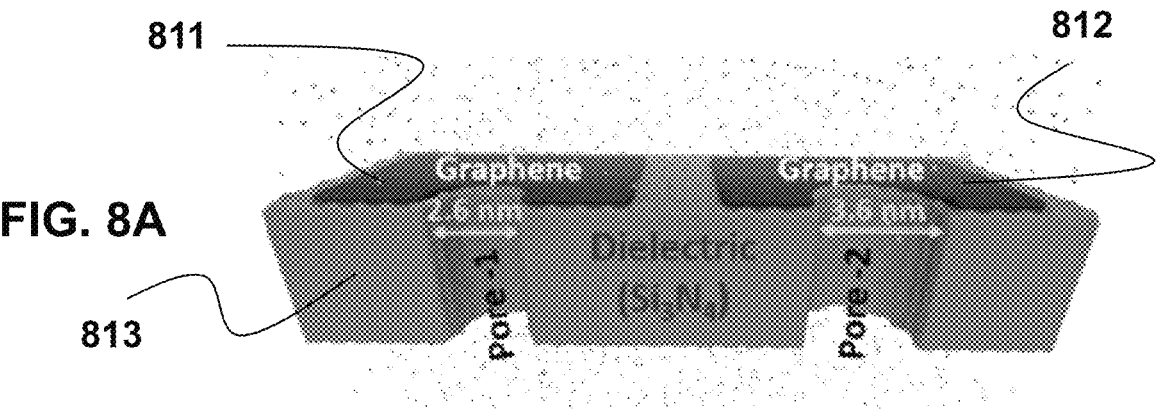
FIGS. 8A and 8B relate to an open-pore MD model according to an embodiment. More particularly.
Figure 8B:
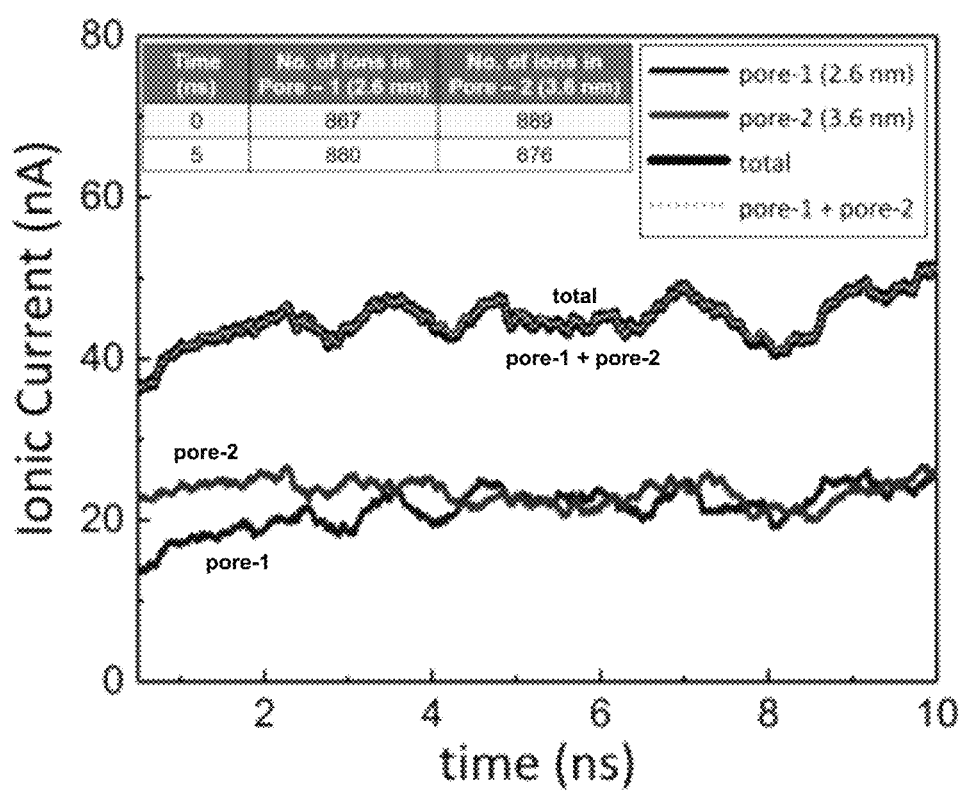
Figure 9:
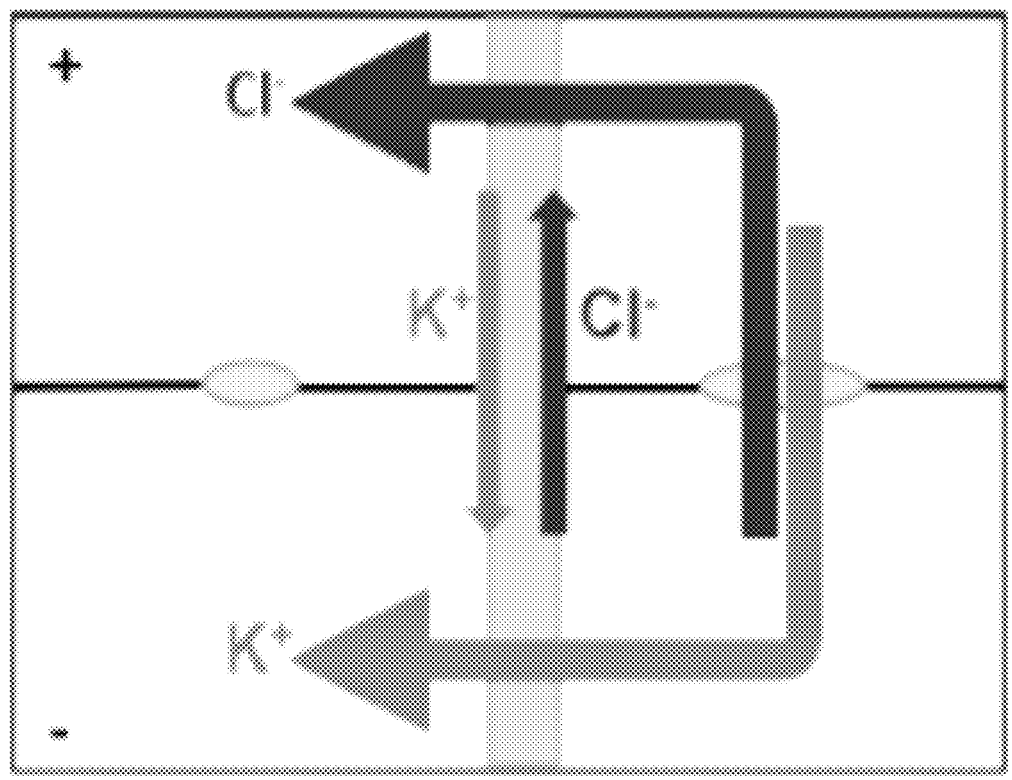
FIG. 9 shows a schematic model representing the flow of ions through a different sized multi-pore system according to an embodiment.

A similar setup is considered to analyze the open-pore behavior for a double-pore system with two different pore sizes, i.e., in this example—a 2.6 nm diameter pore with a 3.6 nm diameter pore (see FIG. 8A). One observes a behavior similar to the two pores with identical diameters. Interestingly, the ionic current through the bigger (3.6 nm)

pore is found to be higher than the current through the smaller (2.6 nm) pore only during the first 5 ns, but converges afterward to a similar value, which is attributed to the current crosstalk between the two pores. To support this interpretation, calculated were the number of ions present in the cis- and the trans-chambers near each pore at the beginning of the simulation, and after 5 ns when the ionic current through each pore becomes equalizes with one another (see FIG. 8A—inset data Table). Initially (at 0 ns), a large number of ions are found to translocate through the bigger pore compared to the number of ions translocating through the smaller (2.6 nm diameter) pore. A schematic representation of the ion flow in the different sized multi-pore system is displayed in FIG. 9. The ion flow through the bigger pore then merges within the cis- and trans-chambers of the whole system making the concentration of ions on either side of the graphene membranes constant after a certain time (namely at 5 ns). No such crosstalk is found with the identical sized multi-pore model as the rate of flow of ions through each pore remained constant throughout the simulation.

Figure 2C:
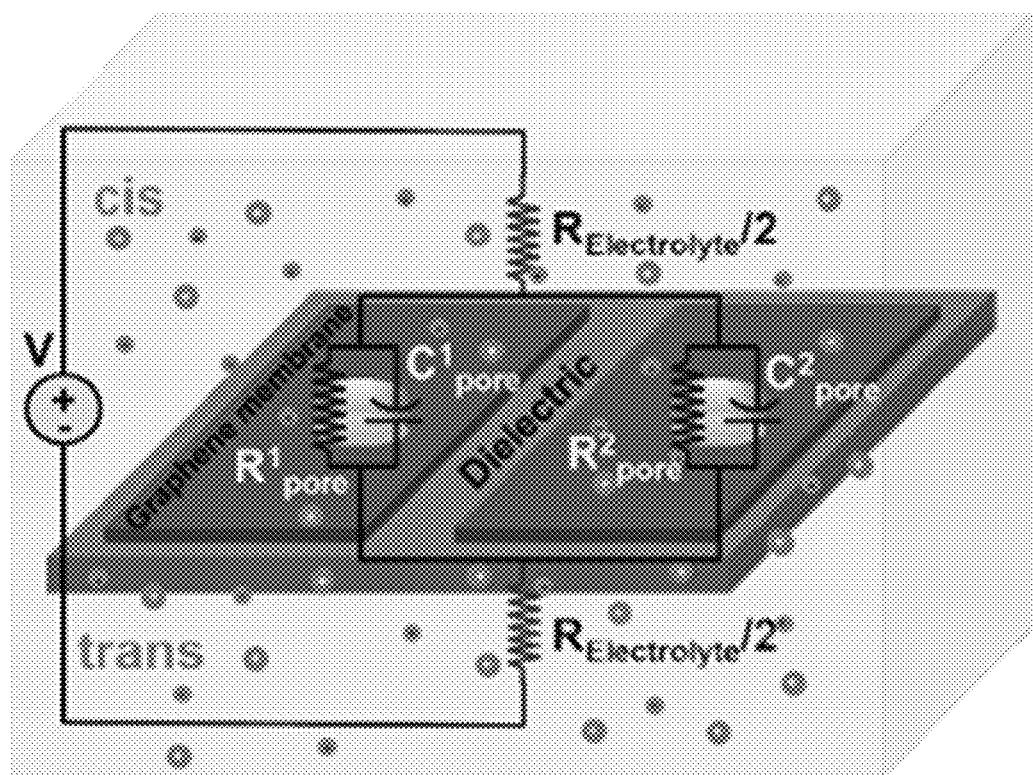
FIG. 2C shows a schematic drawing of a multipore system formulated as a parallel resistor circuit with each nanopore having its respective pore resistance and pore capacitance.

It is known that a nanopore membrane is characterized by a pore resistance and pore capacitance in the cis- and trans-chambers of the ionic box (see generally references 29-34). So, in this example, the multi-pore system is modeled as a parallel RC circuit composed of pore and access components ($R_{pore}$ and $C_{pore}$, respectively). FIG. 2C depicts the schematic of a series resistor model of the double-pore system, where the two graphene nanopore membranes are placed on a dielectric immersed in an ionic solution. Previously, it was found that the ionic conductance blockade ($\Delta G$) strongly decreases with increasing pore diameter (see generally reference 29). However, since the pore diameter of certain examples is considered to be 2.6 nm for all the membranes, $\Delta G$ is expected to remain the same in these examples.

Figure 3A:
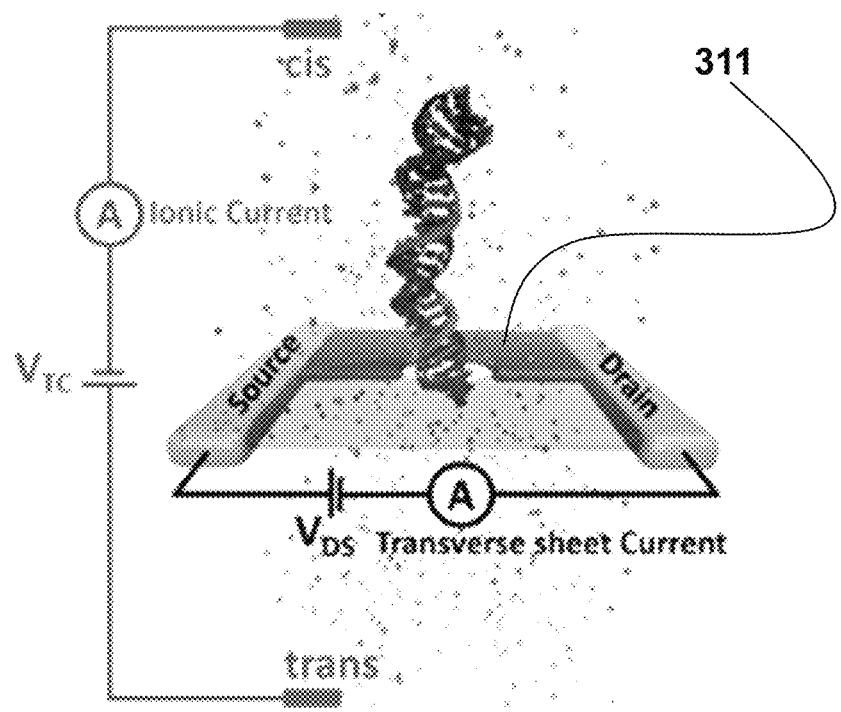
FIGS. 3A and 3B relate to a system setup for DNA detection with graphene nanopore according to an embodiment. More particularly.
Figure 3B:
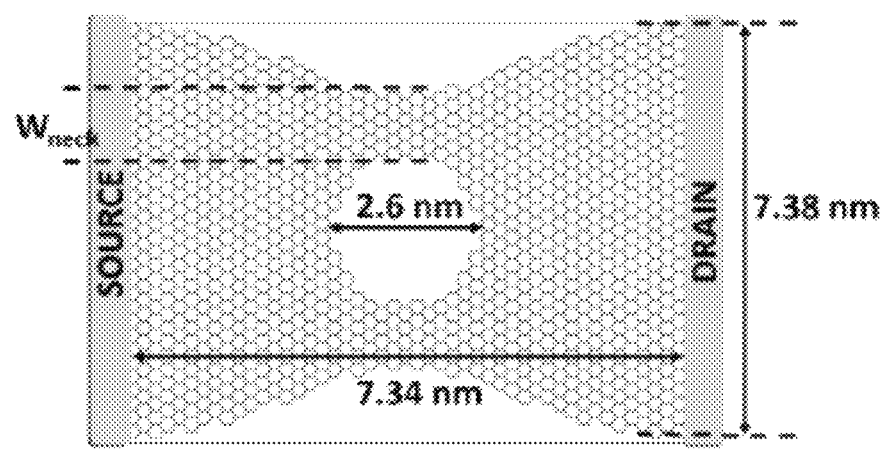

For the sake of illustrating the operation of DNA sensing through the double-pore system according to an embodiment, first obtained are the ionic and transverse electronic sheet currents for a dsDNA molecule translocating through a 2.6 nm pore with different initial conformations in the same system as mentioned above. In order to reduce the computational time of MD simulations, the system is setup with a double stranded DNA (dsDNA) of 25 (A-T) base pairs (bp) long in an ionic solution with a concentration of 0.3 M as shown in FIG. 3A; the applied voltage bias across the cis- and trans-chambers is $V_{TC}=750$ mV. The DNA molecule is placed just above the pore to ensure a direct translocation. The system is minimized and equilibrated before obtaining the final trajectory. With the approach described below, first obtained are the electrostatic potentials via the self-consistent Poisson-Boltzmann equation, which is also used to calculate the transverse electronic sheet current by the nonequilibrium Green's function (NEGF) formalism (see generally reference 25). The graphene nanoribbon is configured into a quantum point contact (g-QPC) geometry with adequate pore shape, position and dimensions to obtain good device sensitivity (see generally references 25,35,36). For a 2.6 nm diameter pore placed at the center of graphene membrane, it was found that a g-QPC of width 7.38 nm and length 7.34 nm (see FIG. 3B) results in a reliable transmission coefficient. The width of the membrane near the neck, denoted as $W_{neck}$, is set to be 1.2 nm.

Figure 10:
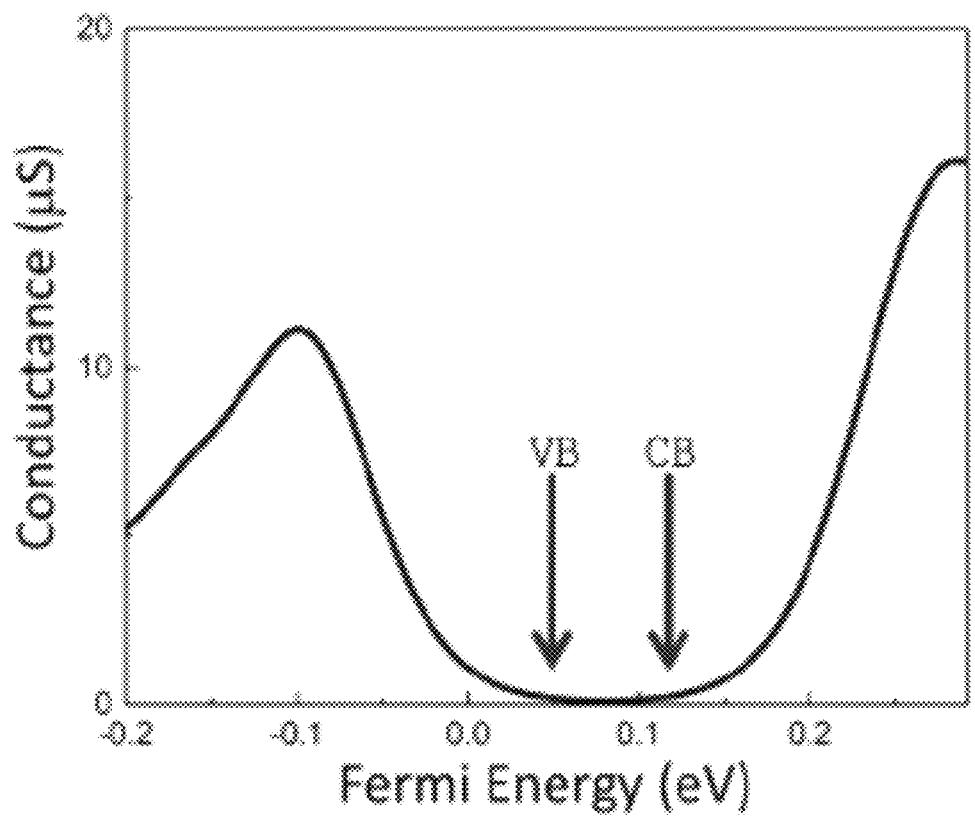
FIG. 10 shows a plot, according to an embodiment, of the electronic conductance versus the carrier Fermi energy for a graphene-QPC with 2.6 nm diameter pore, as calculated from Equation 7 below. Here, the conduction band edge (CB) and the valence band edge (VB) are located at $E_F=0.11$ eV and $E_F=0.05$ eV, respectively, for a band gap of $E_G=0.06$ eV. Therefore, there exists a smooth conductance transition below the gap in the energy interval 0.07 eV-0.1 eV that reveals the presence of mid-gap electronic states contributing to the g-QPC conductance.

Furthermore, for the same g-QPC geometry, the variations of the transverse electronic sheet currents caused by the DNA translocation through the nanopore, as calculated by NEGF, exhibit high detection sensitivity (i.e. $dG/dE_F$) for a graphene Fermi energy ($E_F$) window between 0.1 eV to 0.27 eV in the conduction band (see FIG. 10). Here, the transverse sheet current is obtained for electrons with Fermi energy of 0.14 eV, which displays good conductance variation corresponding to the change in the electrostatic potential variation for both DNA trajectories. A higher carrier Fermi energy (i.e. ≳0.2 eV) would result in an unrealistic gate voltage value as estimated by $en=C_D(V_G-V_T)$, where n is the carrier concentration, $C_D$ is the g-QPC membrane capacitance (high-k dielectrics is considered), $V_G$ is the gate bias, and $V_T$ is the threshold voltage (see generally reference 25). Hence (according to an embodiment), for any given graphene nanopore, the membrane can be tuned to achieve higher sensitivity by changing the gate voltage to position the graphene Fermi level among the midgap states (see generally references 25,36). Since each graphene QPC in the double-pore system (according to an embodiment) has the advantage of achieving higher detection sensitivity by gate voltage variation, the entire system can be optimized by electric tuning of each individual graphene membrane to accurately detect the DNA molecule going through the nanopore. In addition (according to an embodiment), defective nanopore membrane (g-QPC with many geometrical defects rendering unusual behavior of the device) can be identified and separated from the rest of the current signals, similarly as proceeded with defective CMOS integrated circuits.

Figure 4A:
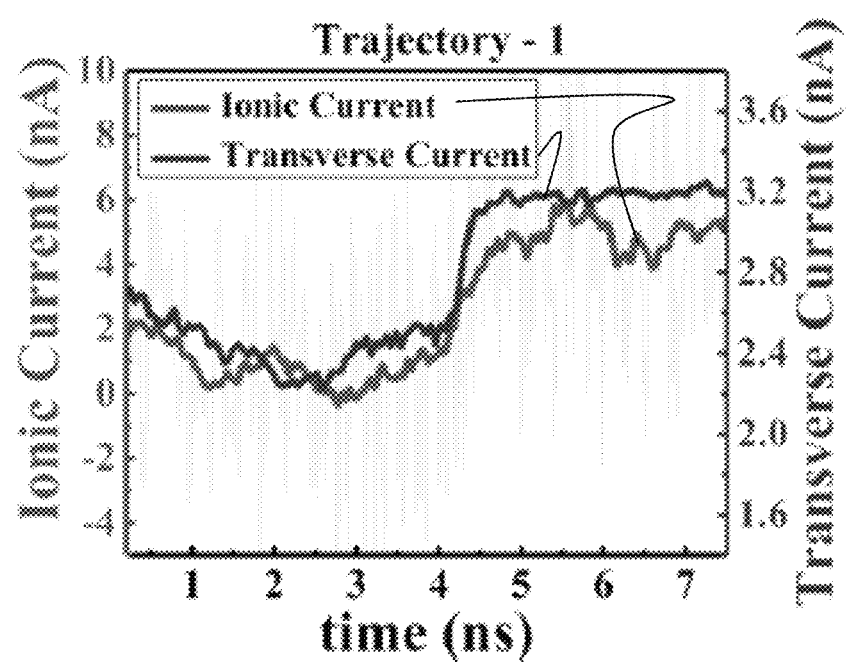
FIGS. 4A and 4B relate to ionic and transverse sheet current signals for DNA translocations according to an embodiment. More particularly.
Figure 4B:
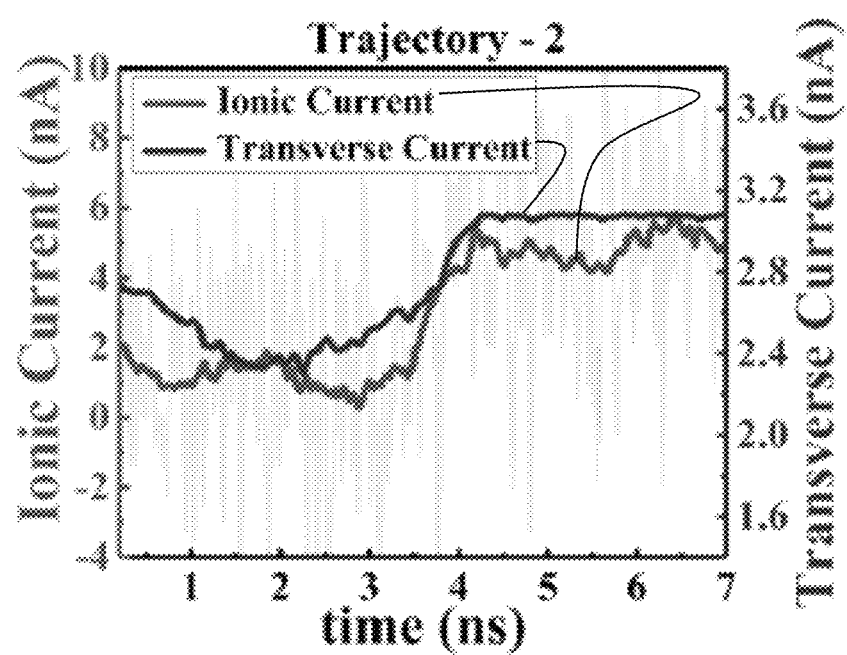

Referring now to FIGS. 4A and 4B, these figures display the ionic and transverse sheet current calculated from two trajectories of DNA translocation through a 2.6 nm pore. Here, different current traces are observed for the two trajectories due to the different conformations of DNA translocating through each pore. Interestingly, in both plots, there is a significant correlation between the transverse electronic sheet current and the ionic current during the blocking event. Once the DNA exits the nanopore, the g-QPC conductance, and consequently the transverse sheet current are significantly influenced by the presence of the DNA near the vicinity of the pore (see generally reference 25), unlike the ionic current resulting from the ion flow through the pore. For this reason, $\Delta G_{ionic}$ (variation of ionic conductance) is greater than $\Delta G_{sheet}$ (variation of graphene electronic sheet conductance).

Figure 5A:
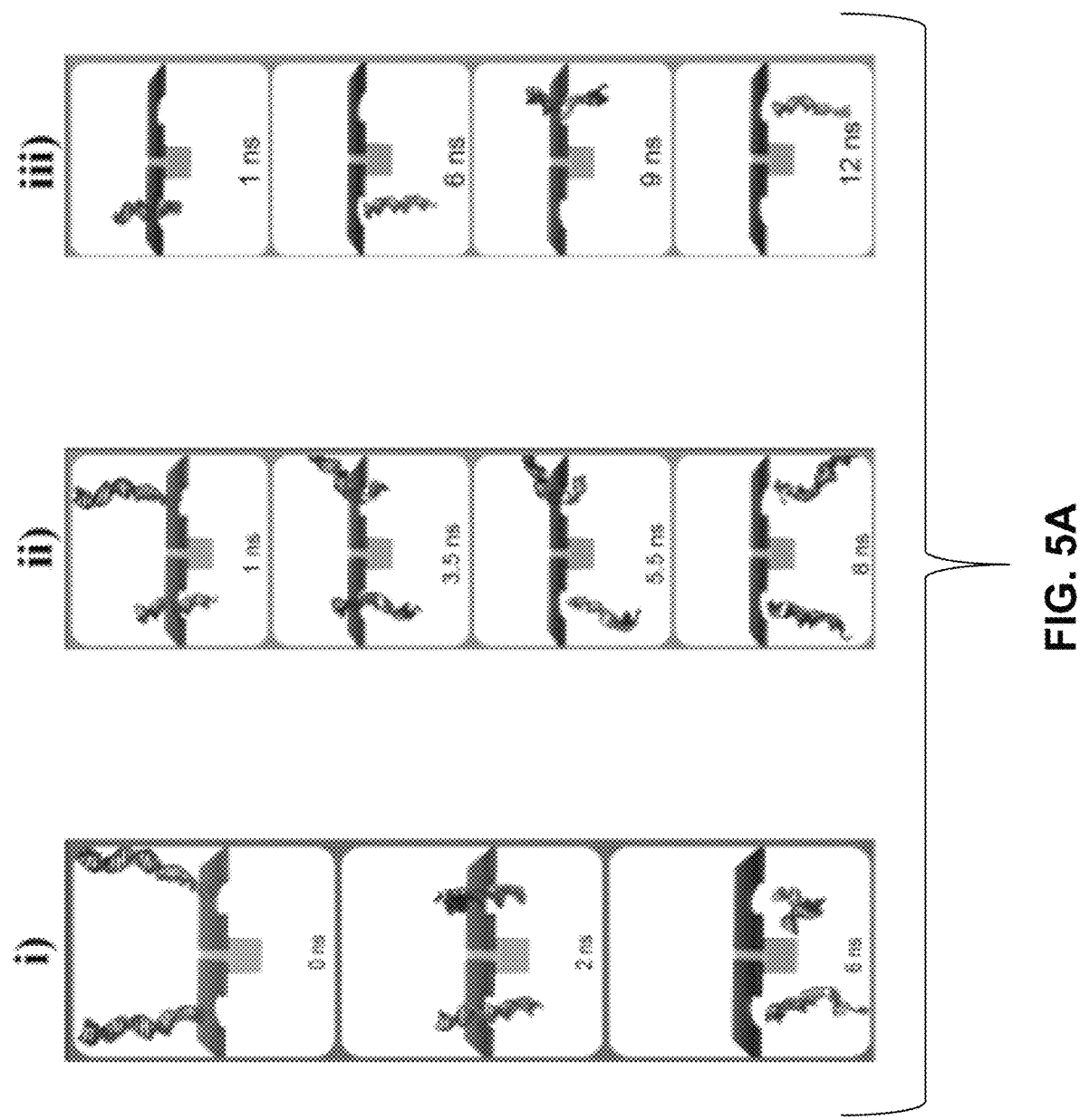
FIGS. 5A and 5B relate to simultaneous detection of multiple dsDNA in a multipore system according to an embodiment. More particularly.
Figure 5B:
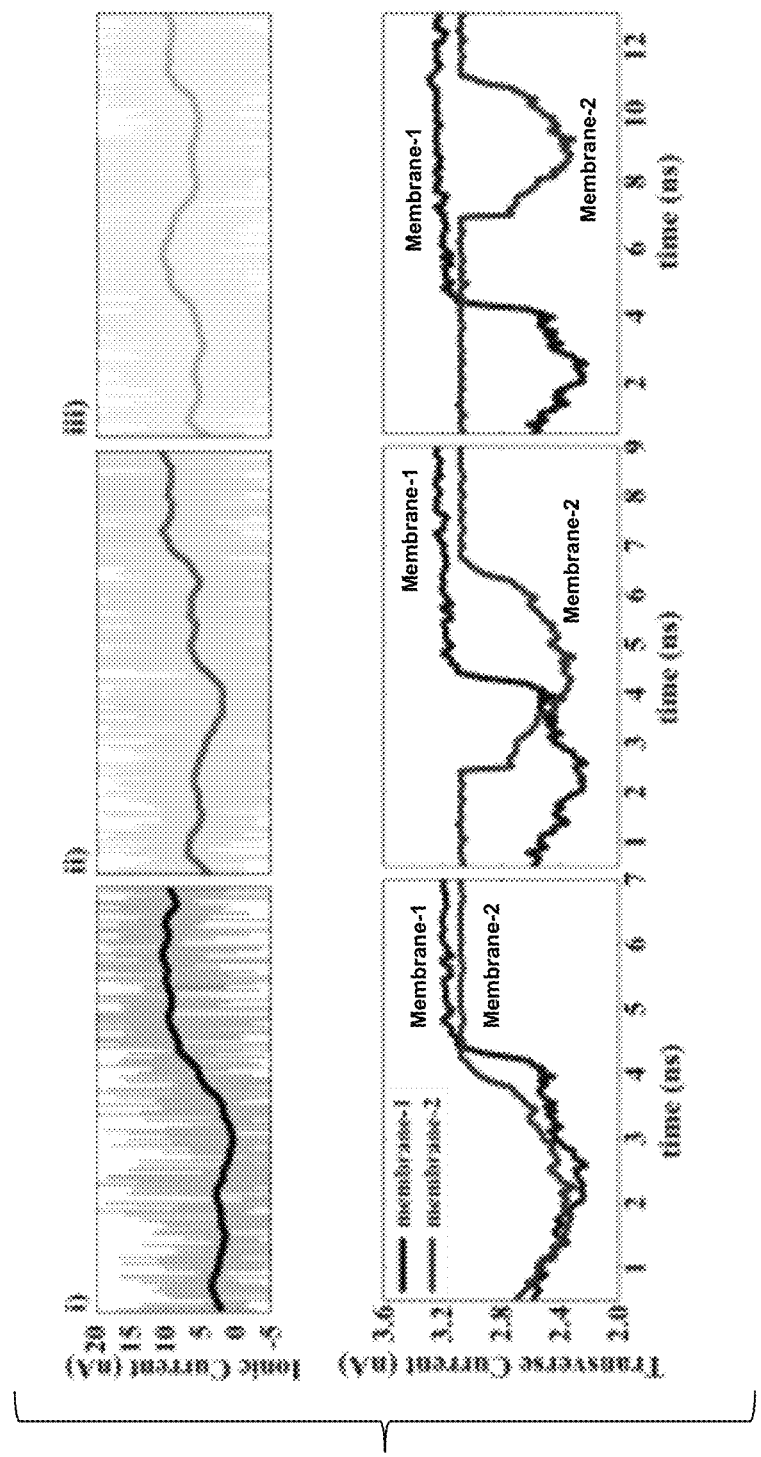

Now considered are three DNA translocation situations that illustrate the concurrent DNA sensing (according to an embodiment) by using the series resistor model: (i) simultaneous DNA translocation through both nanopores (see FIG. 5A, the "i" column), (ii) DNA translocation at two different times with a time overlap between the two events (see FIG. 5A, the "ii" column), and (iii) complete DNA translocation through one nanopore followed by a translocation through the other nanopore (see FIG. 5A, the "iii" column). In FIG. 5B, shown are the ionic and transverse electronic sheet currents obtained from the individual graphene membranes in the three cases (mentioned above—i.e., "i", "ii", "iii"). In all calculations of the sheet current, a carrier Fermi energy of 0.14 eV was considered in the graphene membranes with a source-drain voltage, $V_{DS}=5$ mV at a system temperature of 300 K.

For case (i), the total ionic current, which is the sum of the individual ionic current through each nanopore is shown in FIG. 5B (column "i", top row). FIG. 5B (column "i", bottom row) depicts the transverse electronic sheet current obtained separately for each nanopore membrane, providing distinct current traces for the translocation event. Though the blocking ionic current signal indicates nanopores are obstructed by DNA (by comparing the magnitude of blockade current with the open-pore current), the blocking ionic current signal is, however, unable to detect the individual DNA that translocated through the pores, as it only displays the overall event through the two pores. On the contrary, because of the individual electric connections across each g-QPC membrane of this embodiment, the transverse electronic sheet current has the ability to detect individual translocation through each pore.

FIG. 5B (column "ii", top and bottom rows) display the respective ionic and transverse sheet current traces of a double-pore system, where the DNA translocation event through each pore occurs with a time offset (case ii). Initially, a dsDNA starts translocating through pore-1, while pore-2 is open. 3 ns later, another dsDNA begins its translocation through pore-2 for which observed is a dip in the ionic current, caused by the blockage of both pores. The sheet current traces show an equivalent dip in current through membrane-2 indicating the start of translocation through pore-2. After 5 ns, the dsDNA through pore-1 has completed its translocation, resulting in an increase in both the ionic current and the sheet current through membrane-1. This is subsequently followed by another increase of both currents to the open-pore current of the system at ~7 ns representative of the completion of dsDNA translocation through pore-2.

The final case (iii) for which translocation through pore-1 is followed by another one in pore-2 is shown in FIG. 5B (column "iii", top and bottom rows). Two distinct dips in the ionic current at different time intervals i.e. 0 to 4 ns, and 7 to 11 ns respectively correspond to translocation events of dsDNA through each pore. One sees that the calculated sheet current across the graphene membrane through pore-1 displays a dip (at 0 ns) and rise (at 4 ns) corresponding to the DNA translocation followed by an open-pore. The sheet current remains at ~3.2 nA after 4 ns as there are no other DNA going through the pore that can affect the conductance of graphene. Similarly, the sheet current through the membrane containing pore-2 dips from 7 to 11 ns and remains at ~3.0 nA (open-pore current) for the rest of the time.

Figure 11A:
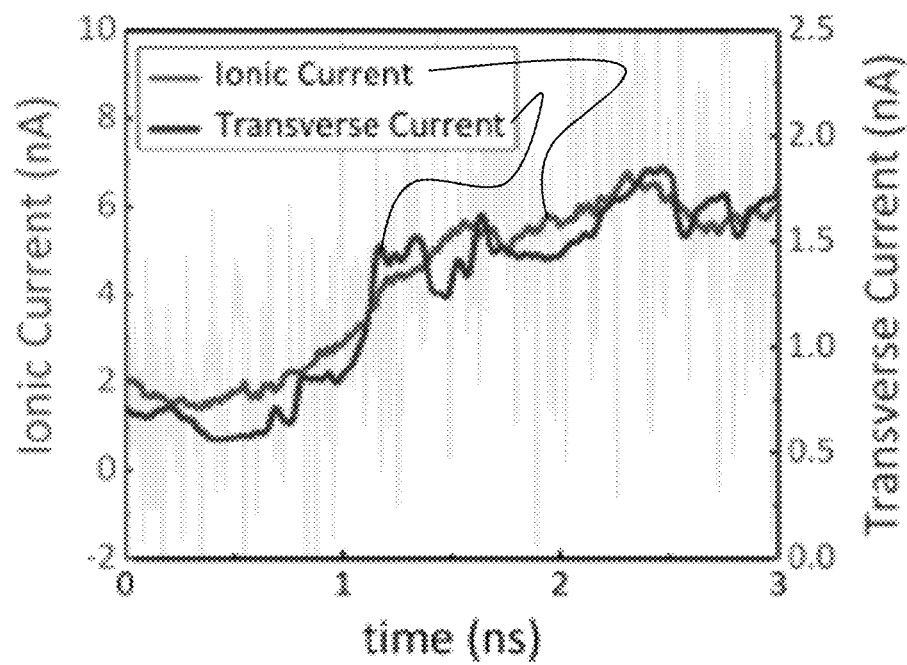
FIGS. 11A and 11B relate to ionic and transverse sheet current obtained according to an embodiment. More particularly.

Reference will now be made to the performance (according to an embodiment) of a similar analysis on a system with two pores of different diameters, i.e. 2.6 nm and 3.6 nm in this example. First, the ionic current and transverse sheet current were obtained for a dsDNA translocating through the 3.6 nm diameter pore (see FIG. 11A). Here, it is observed that the DNA translocation occurs much quicker (at ~1.6 ns) compared to the previous example with a smaller pore, as the pore resistance is negligible. Hence, it is also noticed that the open-pore ionic current is ~6 nA, which is larger compared to the open-pore current of the 2.6 nm pore. Since the resistance scales as 1/d (where d is the diameter of the pore) from 2.6 nm to 3.6 nm pore and not as $1/d^2$, it is concluded that access resistance dominates with bigger pore diameter. This analysis is consistent with previous studies (see generally references 16,29). Furthermore, one sees that ionic current does not have distinct shift between the blocking and open-pore signal as in the case of 2.6 nm pore signals. This is due to larger DNA fluctuations during its translocation in the bigger pore and the presence of DNA having relatively smaller effect to the change in ionic conductance.

Figure 11B:
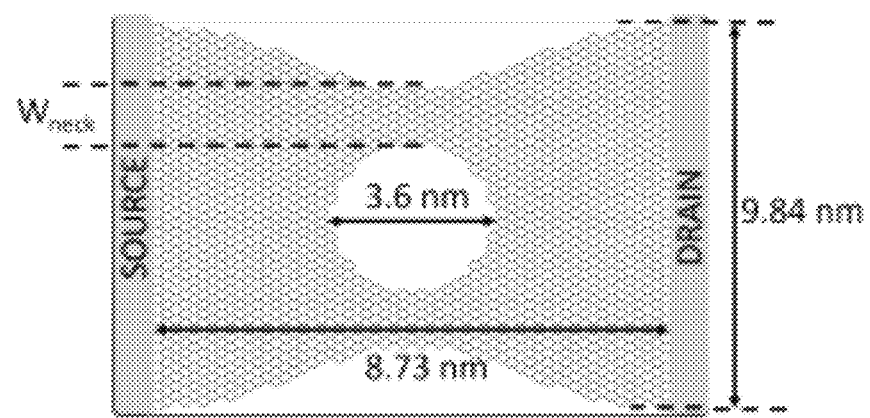

For transverse sheet current calculations, $W_{neck}$ of the g-QPC is set to be equal to 1.2 nm, as for the 2.6 nm pore (see FIG. 11B). Analysis shows that the sheet current exhibits a higher detection sensitivity within the carrier Fermi energy window of 0.04 eV to 0.14 eV. For this reason, the current signal at a Fermi energy of 0.08 eV for electronic carriers in the membrane was considered. The magnitude of the sheet current was found to be smaller compared to the one in the g-QPC with the 2.6 nm pore. Additionally, the sensitivity of the device is highly dependent on the geometry of the QPC and the angular position of DNA in the nanopore during translocation (see generally reference 25) For the corresponding QPC geometry with 3.6 nm pore, a change in the carrier Fermi energy from 0.04 eV to 0.08 eV in the membrane results in a fourfold decrease in the conductance magnitude. On the contrary, for the QPC with the 2.6 nm pore, calculations show a threefold increase in conductance with increasing Fermi energy from 0.10 eV to 0.14 eV in the membrane, which indicated the high sensitivity of the electronic conductance g-QPC with Fermi energy variation.

Figure 6:
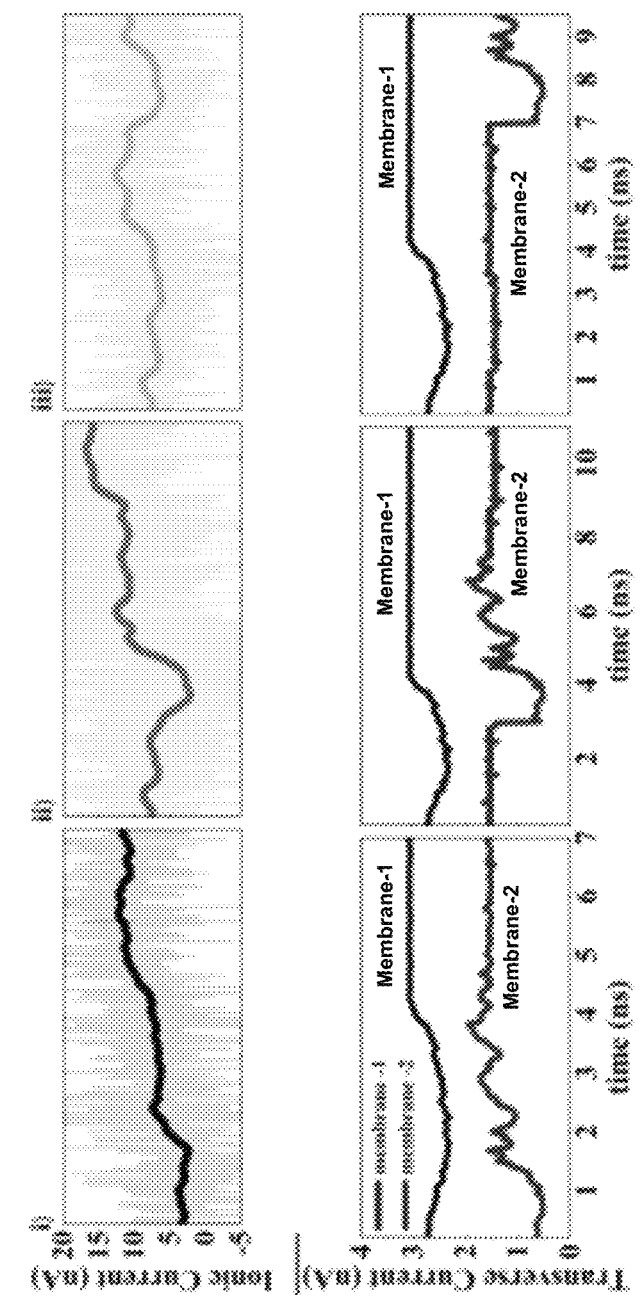
FIG. 6 relates to detection of multiple dsDNA in a nonhomogeneous multipore setup according to an embodiment. More particularly, this

Certain current data obtained for the 3.6 nm diameter pore along with the corresponding current data of trajectory-1 for the 2.6 nm pore is used to investigate three cases of ionic and transverse sheet current for a double-pore system with 2.6 nm and 3.6 nm diameter pores (see FIG. 6, panels i, ii, and iii of the top row of plots and panels i, ii, and iii of the bottom row of plots). The plots are very much like the ones obtained for same sized double-pore system (see FIG. 5B) indicating the concurrent detection of the DNA by transverse sheet current irrespective of the pore non-homogeneity.

Reference will now be made to certain System Setup according to an embodiment. In the MD simulations, graphene membranes of dimensions 9 nm×9 nm were built using Nanostructure Builder plugin in Visual Molecular Dynamics software, VMD (37). For open-pore simulations, the graphene sheets were placed on a 5-nm thick Silicon Nitride ($Si_3N_4$) to restrict the ion flow only through the nanopores. The $Si_3N_4$ was built using the Inorganic Builder plugin in VMD. To obtain a nanopore at the center of the membrane either in graphene alone or in graphene housed on $Si_3N_4$, pore is drilled by removing the atoms whose coordinates satisfy the condition $x^2+y^2 \le r^2$, where r is the radius of the pore. Periodic boundary conditions along the z-direction were assumed to all the nanopore membranes present in the respective simulations. In the simulations, a 25 base-pair double-stranded B-DNA translocating through nanopores was modeled using 3D-DART web server (see generally reference 38). All the systems were solvated in a water box with either 1.0 M (open-pore simulations) or 0.3 M (DNA translocation simulations) KCl using Solvate plugin in VMD.

Reference will now be made to a Molecular Dynamics Protocol according to an embodiment. The MD simulations were performed using NAMD (see generally reference 39). The simulations were analyzed and visualized using VMD (37). The dsDNA was described using CHARMM27 force field (see generally reference 40). The carbon atoms in graphene were treated as CA type atoms (Benzene) in the CHARMM27 force field. Boundaries of the graphene membrane were restrained using harmonic forces with spring constant of 10 Kcal $mol^{-1}$ to prevent drifting. Water was modeled as TIP3P water model (see generally reference 41). Periodic boundary conditions were employed in all directions. Van der Waals energies were calculated using a 12 Å cutoff. A time step of 2 fs with Particle Mesh Ewald of grid size 96×96×256 (X×Y×Z) to treat long-range electrostatics (see generally reference 42) was implemented. A Langevin thermostat was used to maintain constant temperature at 300 K. The system consisted of ~162,000 atoms, of which ~156,000 atoms were water and ~600 atoms of ions ($K^+$ and $Cl^-$). All the systems were minimized for 5,000 steps, followed by a 600 ps equilibration as NPT ensemble. During equilibration, the pressure was maintained at 1 atm by a Langevin piston (see generally reference 43) for pressure control and Langevin dynamics for temperature control. Next, the system was further equilibrated for 2 ns in an NVT ensemble. Finally, an electric field, E=V/$L_z$, was applied to the system in +z direction to drive the DNA through the nanopore, where V is the voltage bias and $L_z$ is the length of the water box in z direction. The voltage bias used for translocation in all the systems was 0.75 V. The low ionic concentration of the system (0.3 M) results in a small number of counter-ions across the surfaces of graphene membrane. In addition, grid forces applied on the surface minimize the interaction of graphene atoms with water and ions to ensure reliable translocations of the DNA. Hence, the capacitive current that arises from the ion buildup on the surface of graphene is negligible at the initial stages of the simulations. The trajectories of all the atoms present in the system were recorded at every 5000 steps until the DNA has completely translocated through the pore. These trajectories were further used to calculate the ionic current and electrostatic potentials for electronic transport calculations.

Reference will now be made to Ionic Current Calculation according to an embodiment. The instantaneous ionic current I(t) through nanopores was calculated using the following relation $$I(t) = \frac{1}{\Delta t L_z} \sum_{i=1}^{N} q_j(z_i(t+\Delta t) - z_i(t)) \quad (1A)$$

where $q_i$ and $z_i$ are the charge and z-coordinate of ion i, respectively. N represents the number of ions and $L_z$ is the z-coordinate dimension of the entire system. At is the interval between the trajectory frames.

For each frame of the trajectory, electrostatic potential (r) is calculated using the self-consistent Poisson-Boltzmann equation:

$$\nabla \cdot [\varepsilon(r) \nabla \varphi(r)] = -e[C_{K+}(r) - C_{Cl-}(r)] - \rho_{DNA}(r) \quad (2A)$$

Where $\rho_{DNA}(r)$ is the charge density of DNA, $\varepsilon(r)$ being the local permittivity, $C_{K+}(r)$ and $C_{Cl-}(r)$ are the local electrolyte concentrations of K+ and Cl− that obey Poisson Boltzmann statistics given by the following equations:

$$C_{K+}(r) = C_0 \exp\left[\frac{-e\phi(r)}{k_u T}\right] \quad (3A)$$

$$C_{Cl-}(r) = C_0 \exp\left[\frac{e\phi(r)}{k_u T}\right] \quad (4A)$$

Here, $C_0$ is the nominal concentration in the solution, which is set to 0.3 M. The above two equations are solved numerically till convergence criteria is met.

The electrostatic potential co-planar to the membrane thus obtained, is incorporated to calculate the Green's function G, using the non-equilibrium Green's function formalism, as described by the following equation.

$$G = \left[(E+i\eta)I - H - \sum_{\alpha}\sum_{\alpha}\right]^{-1} \quad (5A)$$

Where $\Sigma_\alpha \equiv V_{\alpha C}[E-H_\alpha]^{-1}$, $V_{\alpha C}$ is the 'self-energy' of lead $\alpha$, I the Identity matrix, $\eta$ is a small value in the order of $10^{-28}$ to avoid singularities in the computation and H is the tight-binding Hamiltonian. Utilized are the third nearest neighbor and three orbital interaction Hamiltonian in the calculations. The edges of the graphene membrane are passivated with Hydrogen.

From the Green's function, G, obtained is the transmission coefficient $\bar{T}(E)$ between leads 1 and 2 by the following equation ( )TE $$\bar{T}(E) = -Tr[(\Sigma_1 - \Sigma_1^\dagger)G(\Sigma_2 - \Sigma_2^\dagger)G^\dagger] \quad (6A)$$

Finally, the transverse conductance across the 2D nanopore graphene QPC for a given source-drain bias, $V_{DS}$, is calculated using $$G = \frac{2e}{V_{DS}h}\int_{-\infty}^{\infty}\bar{T}(E)[f_1(E)-f_2(E)]dE \quad (7A)$$

Here, $f_\alpha(E) = f(E-\mu_\alpha)$ is the probability of an electron occupying a state at energy E in the lead $\alpha$, and $V_{DS}=(\mu_1-\mu_2)/e$ is the bias across the conductor.

In the present study, used is a source-drain voltage, $V_{DS}=5$ mV at a system temperature of 300 K. In this model, ignored is the effect of surface charges that arise when the graphene encounters water. In certain graphene nanopore devices according to various embodiments, additional oxide layers can be used, sandwiching the graphene layer, thereby preventing the graphene layer from coming in direct contact with the solution.

Referring now to FIG. 12, various steps of a method 1200 according to an embodiment are shown. As seen in this FIG. 12, step 1202 comprises sensing, by a processing system including a processor, a first characteristic associated with a first translocation of a first biomolecule (such as DNA or RNA) through a first pore of a first membrane of a plurality of membranes, wherein the first membrane is disposed on a dielectric substrate, wherein the first pore goes through the first membrane, wherein the first pore is associated with a corresponding first hole that extends through the dielectric substrate, and wherein the first membrane is in electrical contact with a first pair of electrodes via which the first characteristic is sensed. Next, step 1204 comprises sensing, by the processing system, a second characteristic associated with a second translocation of a second biomolecule (such as DNA or RNA) through a second pore of a second membrane of the plurality of membranes, wherein the second membrane is disposed on the dielectric substrate, wherein the second pore goes through the second membrane, wherein the second pore is associated with a corresponding second hole that extends through the dielectric substrate, wherein the second membrane is not in direct contact with the first membrane, wherein the second membrane is not in electrical contact with the first pair of electrodes, and wherein the second membrane is in electrical contact with a second pair of electrodes via which the second characteristic is sensed.

While for purposes of simplicity of explanation, the respective processes are shown and described as a series of blocks in FIG. 12, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

Referring now to FIG. 13, various steps of a method 1300 according to an embodiment are shown. As seen in this FIG. 13, step 1302 comprises obtaining a first electrical characteristic associated with a first translocation of a first biomolecule (such as DNA or RNA) through a first pore of a first membrane of a plurality of membranes, wherein the first membrane is located on a dielectric substrate, wherein the first pore goes through the first membrane, wherein the first pore is associated with a corresponding first hole that extends through the dielectric substrate, and wherein the first membrane is in electrical contact with a first pair of electrodes via which the first electrical characteristic is sensed. Next, step 1304 comprises obtaining a second electrical characteristic associated with a second translocation of a second biomolecule (such as DNA or RNA) through a second pore of a second membrane of the plurality of membranes, wherein the second membrane is located on the dielectric substrate, wherein the second pore goes through the second membrane, wherein the second pore is associated with a corresponding second hole that extends through the dielectric substrate, wherein the second membrane is not in direct contact with the first membrane, wherein the second membrane is not in electrical contact with the first pair of electrodes, and wherein the second membrane is in electrical contact with a second pair of electrodes via which the second electrical characteristic is sensed.

While for purposes of simplicity of explanation, the respective processes are shown and described as a series of blocks in FIG. 13, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described herein.

In another example, one or more membranes can comprise silicon and/or any other desired semiconductor.

As described herein, various embodiments provide for parallelism in making measurements.

In various embodiments, each of the plurality of membranes is not in electrical contact with any other of the plurality of membranes.

In various embodiments, the plurality of membranes are disposed as an array of x-number of membranes by y-number of membranes (e.g., a 1,000 membrane by 1,000 membrane array).

In one embodiment, an apparatus is provided comprising: a plurality of electrically active membranes positioned on top of a dielectric substrate, wherein each of the plurality of membranes has a first side and a second side, wherein each membrane has a pore disposed therein, wherein the pore extends through the membrane from the first side of the membrane to the second side of the membrane and through the dielectric substrate, wherein the plurality of membranes are not in direct contact with each other, and wherein each individual membrane has a source electrode and a drain electrode capable of analyzing one or more molecules going through the pore. In one example, each of the plurality of membranes is made of a semiconductor material. In another example, the semiconductor material is graphene. In another example, the dielectric substrate is made from a material selected from $Si_3N_4$, $Al_2O_3$, and $SiO_2$. In another example, the apparatus can make simultaneous multi-channel measurements (e.g., measurements related to multiple pores can be made at the same time). In another example, a multi-layer configuration (e.g., a "sandwiched" configuration) can be used. Such a configuration can comprise, for example, a plurality of membranes encapsulated between two dielectric layers (in this configuration the dielectric layers can, for example, protect the membranes (e.g., semiconductor membranes) from the liquid into which the device (all or a portion thereof) is placed.

As described herein according to various embodiments is a scalable device design of a dense array of multiple nanopores made from nanoscale semiconductor materials to detect and identify translocations of many biomolecules in a massively parallel detection scheme. Use of molecular dynamics can be coupled to nanoscale device simulations to illustrate the ability of the device setup to uniquely identify DNA parallel translocations. It is shown in connection with various embodiments that the transverse sheet currents along membranes are immune to the crosstalk effects arising from simultaneous translocations of biomolecules through multiple pores, due to their ability to sense only the local potential changes. It is also shown in connection with various embodiments that electronic sensing across the nanopore membrane offers a higher detection resolution compared to ionic current blocking technique in a multi-pore setup, irrespective of the irregularities that occur while fabricating the nanopores in a 2D membrane.

From the foregoing descriptions, it would be evident to an artisan with ordinary skill in the art that the aforementioned embodiments can be modified, reduced, or enhanced without departing from the scope and spirit of the claims described below. For example, any desired number of membrane/electrode pairs can be utilized. Other suitable modifications can be applied to the subject disclosure. Accordingly, the reader is directed to the claims for a fuller understanding of the breadth and scope of the subject disclosure.

Figure 14:
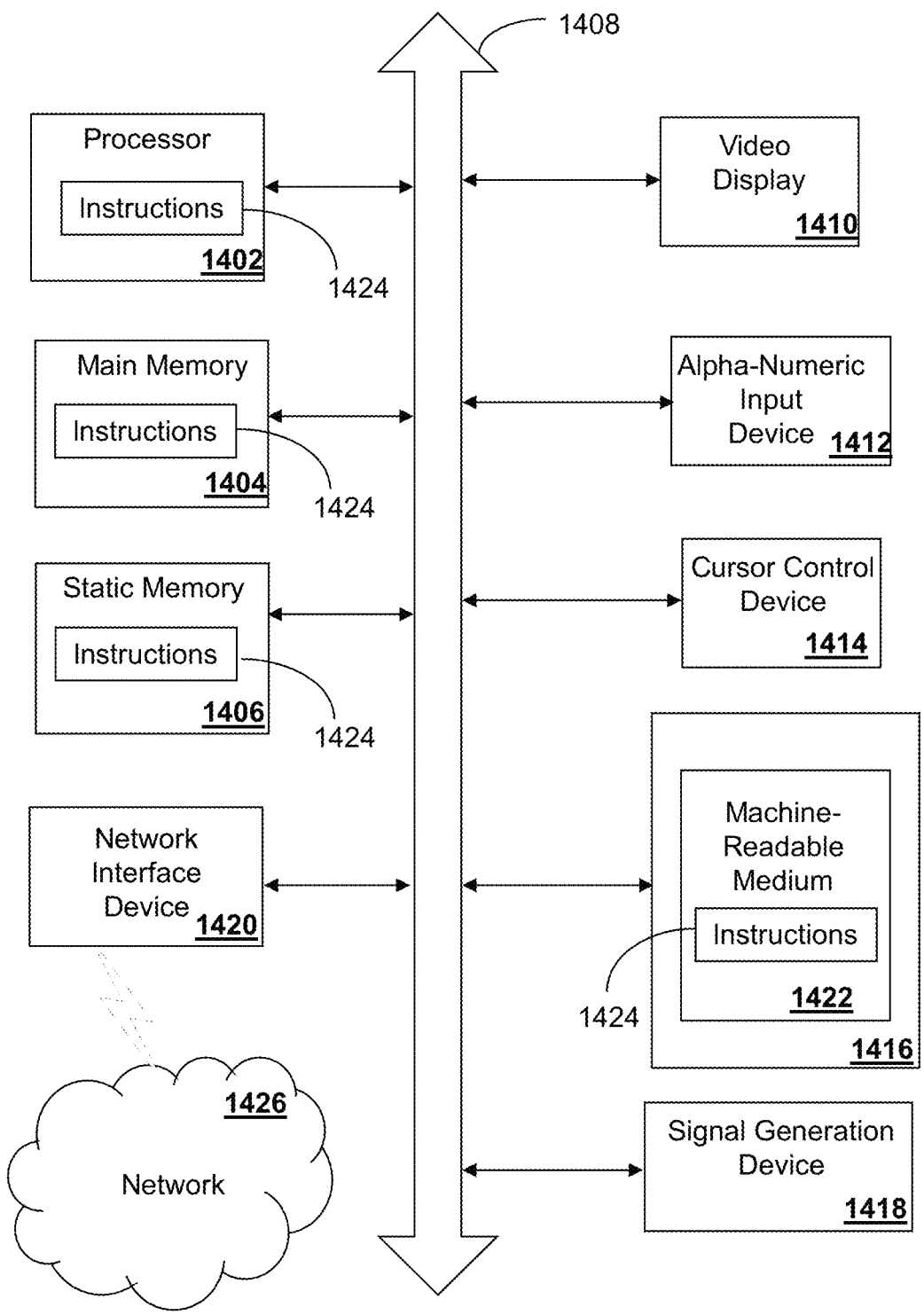
FIG. 14 is a block diagram illustrating an example, non-limiting embodiment of a system in accordance with various aspects described herein.

FIG. 14 depicts an exemplary diagrammatic representation of a machine in the form of a computer system 1400 within which a set of instructions, when executed, may cause the machine to perform any one or more of the methods discussed above. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1400 may include a processor 1402 (e.g., a central processing unit (CPU), a graphics processing unit (GPU, or both), a main memory 1404 and a static memory 1406, which communicate with each other via a bus 1408. The computer system 1400 may further include a video display unit 1410 (e.g., a liquid crystal display (LCD), a flat panel, or a solid state display. The computer system 1400 may include an input device 1412 (e.g., a keyboard), a cursor control device 1414 (e.g., a mouse), a disk drive unit 1416, a signal generation device 1418 (e.g., a speaker or remote control) and a network interface device 1420.

The disk drive unit 1416 may include a tangible computer-readable storage medium 1422 on which is stored one or more sets of instructions (e.g., software 1424) embodying any one or more of the methods or functions described herein, including those methods illustrated above. The instructions 1424 may also reside, completely or at least partially, within the main memory 1404, the static memory 1406, and/or within the processor 1402 during execution thereof by the computer system 1400. The main memory 1404 and the processor 1402 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

While the tangible computer-readable storage medium 1422 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1400.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

REFERENCES (1) Gracheva, M. E.; Xiong, A.; Aksimentiev, A.; Schulten, K.; Timp, 492 G.; Leburton, J.-P. Simulation of the Electric Response of DNA 493 Translocation through a Semiconductor Nanopore-capacitor. Nano-494 technology 2006, 17, 622-633.

(2) Li, J.; Stein, D.; McMullan, C.; Branton, D.; Aziz, M. J.; 496 Golovchenko, J. A. Ion-Beam Sculpting at Nanometre Length Scales. 497 Nature 2001, 412, 166-169.

(3) Dekker, C. Solid-State Nanopores. Nat. Nanotechnol. 2007, 2, 499 209-215.

(4) Siwy, Z.; Fuliński, A. Fabrication of a Synthetic Nanopore Ion 501 Pump. Phys. Rev. Lett. 2002, 89, 198103.

(5) Storm, A. J.; Chen, J. H.; Ling, X. S.; Zandbergen, H. W.; Dekker, 503 C. Fabrication of Solid-State Nanopores with Single-Nanometre 504 Precision. Nat. Mater. 2003, 2, 537-540.

(6) Krapf, D.; Wu, M.-Y.; Smeets, R. M. M.; Zandbergen, H. W.; 506 Dekker, C.; Lemay, S. G. Fabrication and Characterization of 507 Nanopore-Based Electrodes with Radii down to 2 Nm. Nano Lett. 508 2006, 6, 105-109.

(7) Rhee, M.; Burns, M. A. Nanopore Sequencing Technology: 510 Research Trends and Applications. Trends Biotechnol. 2006, 24, 580-511 586.

(8) Gracheva, M. E.; Aksimentiev, A.; Leburton, J.-P. Electrical 513 Signatures of Single-Stranded DNA with Single Base Mutations in a 514 Nanopore Capacitor. Nanotechnology 2006, 17, 3160-3165.

(9) Feng, J.; Graf, M.; Liu, K.; Ovchinnikov, D.; Dumcenco, D.; 516 Heiranian, M.; Nandigana, V.; Alum, N. R.; Kis, A.; Radenovic, A. 517 Single-Layer MoS2 Nanopores as Nanopower Generators. Nature 518 2016, 536, 197-200.

(10) Cohen-Tanugi, D.; Grossman, J. C. Water Desalination across 520 Nanoporous Graphene. Nano Lett. 2012, 12, 3602-3608.

(11) Surwade, S. P.; Smirnov, S. N.; Vlassiouk, I. V.; Unocic, R. R.; 522 Veith, G. M.; Dai, S.; Mahurin, S. M. Water Desalination Using 523 Nanoporous Single-Layer Graphene. Nat. Nanotechnol. 2015, 10, 459-524 464.

(12) Venkatesan, B. M.; Bashir, R. Nanopore Sensors for Nucleic 526 Acid Analysis. Nat. Nanotechnol. 2011, 6, 615-624.

(13) Feng, Y.; Zhang, Y.; Ying, C.; Wang, D.; Du, C. Nanopore-528 Based Fourth-Generation DNA Sequencing Technology. Genomics, 529 Proteomics Bioinf. 2015, 13, 4-16.

(14) Branton, D.; Deamer, D. W.; Marziali, A.; Bayley, H.; Benner, S. 531 A.; Butler, T.; Di Ventra, M.; Garaj, S.; Hibbs, A.; Huang, X.; et al. The 532 Potential and Challenges of Nanopore Sequencing. Nat. Biotechnol. 533 2008, 26, 1146-1153.

(15) Carson, S.; Wanunu, M. Challenges in DNA Motion Control 535 and Sequence Readout Using Nanopore Devices. Nanotechnology 536 2015, 26, 074004.

(16) Schneider, G. F.; Kowalczyk, S. W.; Calado, V. E.; Pandraud, G.; 538 Zandbergen, H. W.; Vandersypen, L. M. K.; Dekker, C. DNA 539 Translocation through Graphene Nanopores. Nano Lett. 2010, 10, 540 3163-3167.

(17) Garaj, S.; Hubbard, W.; Reina, a.; Kong, J.; Branton, D.; 542 Golovchenko, J. a. Graphene as a Subnanometre Trans-Electrode 543 Membrane. Nature 2010, 467, 190-193.

(18) Merchant, C. A.; Healy, K.; Wanunu, M.; Ray, V.; Peterman, N.; 545 Bartel, J.; Fischbein, M. D.; Venta, K.; Luo, Z.; Johnson, A. T. C.; et al. 546 DNA Translocation through Graphene Nanopores. Nano Lett. 2010, 547 10, 2915-2921.

(19) Gadaleta, A.; Sempere, C.; Gravelle, S.; Siria, A.; Fulcrand, R.; 549 Ybert, C.; Bocquet, L. Sub-Additive Ionic Transport across Arrays of 550 Solid-State Nanopores. Phys. Fluids 2014, 26, 012005.

(20) Pud, S.; Chao, S. H.; Belkin, M.; Verschueren, D.; Huijben, T.; 552 Van Engelenburg, C.; Dekker, C.; Aksimentiev, A. Mechanical 553 Trapping of DNA in a Double-Nanopore System. Nano Lett. 2016, 554 16, 8021-8028.

(21) Hall, J. E. Access Resistance of a Small Circular Pore. J. Gen. 555 Physiol. 1975, 66, 531-532.

(22) Postma, H. W. C. Rapid Sequencing of Individual DNA 557 Molecules in Graphene Nanogaps. Nano Lett. 2010, 10, 420-425.

(23) Prasongkit, J.; Grigoriev, A.; Pathak, B.; Ahuja, R.; Scheicher, R. H. Transverse Conductance of DNA Nucleotides in a Graphene 560 Nanogap from First Principles. Nano Lett. 2011, 11, 1941-1945.

(24) Avdoshenko, S. M.; Nozaki, D.; Gomes da Rocha, C.; Gonzalez, J. W.; Lee, M. H.; Gutierrez, R. R.; Cuniberti, G. Dynamic and 563 Electronic Transport Properties of DNA Translocation through 564 Graphene Nanopores. Nano Lett. 2013, 13, 1969-1976.

(25) Girdhar, A.; Sathe, C.; Schulten, K.; Leburton, J.-P. Graphene 566 Quantum Point Contact Transistor for DNA Sensing. Proc. Natl. Acad. 567 Sci. U.S.A 2013, 110, 16748-16753.

(26) Saha, K. K.; Drndić, M.; Nikolić, B. K. DNA Base-Specific 569 Modulation of Microampere Transverse Edge Currents through a 570 Metallic Graphene Nanoribbon with a Nanopore. Nano Lett. 2012, 12, 571 50-55.

(27) Traversi, F.; Raillon, C.; Benameur, S. M.; Liu, K.; Khlybov, S.; 573 Tosun, M.; Krasnozhon, D.; Kis, A.; Radenovic, A. Detecting the 574 Translocation of DNA through a Nanopore Using Graphene 575 Nanoribbons. Nat. Nanotechnol. 2013, 8, 939-945.

(28) Heerema, S. J.; Vicarelli, L.; Pud, S.; Schouten, R. N.; 577 Zandbergen, H. W.; Dekker, C. Probing DNA Translocations with 578 Inplane Current Signals in a Graphene Nanoribbon with a Nanopore. 579 ACS Nano 2018, 12, 2623-2633.

(29) Kowalczyk, S. W.; Grosberg, A. Y.; Rabin, Y.; Dekker, C. 581 Modeling the Conductance and DNA Blockade of Solid-State 582 Nanopores. Nanotechnology 2011, 22, 315101.

(30) Hyun, C.; Rollings, R.; Li, J. Probing Access Resistance of Solid—584 State Nanopores with a Scanning-Probe Microscope Tip. Small 2012, 585 8, 385-392.

(31) Wang, J.; Ma, J.; Ni, Z.; Zhang, L.; Hu, G. Effects of Access 587 Resistance on the Resistive-Pulse Caused by Translocating of a 588 Nanoparticle through a Nanopore. RSC Adv. 2014, 4, 7601-7610.

(32) Xie, P.; Xiong, Q.; Fang, Y.; Qing, Q.; Lieber, C. M. Local 590 Electrical Potential Detection of DNA by Nanowire-Nanopore 591 Sensors. Nat. Nanotechnol. 2012, 7, 119-125.

(33) Bezrukov, S. M.; Vodyanoy, I. Probing Alamethicin Channels 593 with Water-Soluble Polymers. Effect on Conductance of Channel 594 States. Biophys. J. 1993, 64, 16-25.

(34) Dimitrov, V.; Mirsaidov, U.; Wang, D.; Sorsch, T.; Mansfield, 596 W.; Miner, J.; Klemens, F.; Cirelli, R.; Yemenicioglu, S.; Timp, G. 597 Nanopores in Solid-State Membranes Engineered for Single Molecule 598 Detection. Nanotechnology 2010, 21, 065502.

(35) Girdhar, A.; Sathe, C.; Schulten, K.; Leburton, J.-P. Tunable 600 Graphene Quantum Point Contact Transistor for DNA Detection and 601 Characterization. Nanotechnology 2015, 26, 134005.

(36) Sarathy, A.; Qiu, H.; Leburton, J.-P. Graphene Nanopores for 603 Electronic Recognition of DNA Methylation. J. Phys. Chem. B 2017, 604 121, 3757-3763.

(37) Humphrey, W.; Dalke, A.; Schulten, K. VMD—Visual 606 Molecular Dynamics. J. Mol. Graphics 1996, 14, 33-38.

(38) van Dijk, M.; Bonvin, A. M. J. J. 3D-DART: A DNA Structure 608 Modelling Server. Nucleic Acids Res. 2009, 37, W235-W239.

(39) Phillips, J. C.; Braun, R.; Wang, W.; Gumbart, J.; Tajkhorshid, 610 E.; Villa, E.; Chipot, C.; Skeel, R. D.; Kale, L.; Schulten, K. Scalable 611 Molecular Dynamics with NAMD. J. Comput. Chem. 2005, 26, 1781-612 1802.

(40) MacKerell, A. D.; Bashford, D.; Bellott, M.; Dunbrack, R. L.; 614 Evanseck, J. D.; Field, M. J.; Fischer, S.; Gao, J.; Guo, H.; Ha, S.; et al. 615 All-Atom Empirical Potential for Molecular Modeling and Dynamics 616 Studies of Proteins. J. Phys. Chem. B 1998, 102, 3586-3616.

(41) Jorgensen, W. L.; Chandrasekhar, J.; Madura, J. D.; Impey, R. 618 W.; Klein, M. L. Comparison of Simple Potential Functions for 619 Simulating Liquid Water. J. Chem. Phys. 1983, 79, 926-935.

(42) Essmann, U.; Perera, L.; Berkowitz, M. L.; Darden, T.; Lee, H.; 621 Pedersen, L. G. A Smooth Particle Mesh Ewald Method. J. Chem. Phys. 622 1995, 103, 8577-8593.

(43) Feller, S. E.; Zhang, Y.; Pastor, R. W.; Brooks, B. R. Constant Pressure Molecular Dynamics Simulation: The Langevin Piston Method. J. Chem. Phys. 1995, 103, 4613-4621.

What is claimed is:

1. An apparatus comprising:
a dielectric substrate;
a plurality of membranes comprising at least a first membrane and a second membrane, wherein each of the plurality of membranes is positioned upon the dielectric substrate, wherein each of the plurality of membranes has a first side and a second side, wherein each of the plurality of membranes has a pore disposed therein, wherein each pore extends through each respective membrane from the first side of the respective membrane to the second side of the respective membrane, wherein each pore is associated with a corresponding hole that extends through the dielectric substrate, and wherein a physical gap exists between the first membrane and the second membrane such that the first membrane is not in direct contact with the second membrane; and
a plurality of electrode pairs, wherein each of the plurality of electrode pairs is in contact with a single respective one of the plurality of membranes.

2. The apparatus of claim 1, wherein each of the plurality of membranes comprises a semiconductor material.

3. The apparatus of claim 2, wherein the semiconductor material comprises a two-dimensional material.

4. The apparatus of claim 3, wherein the two-dimensional material comprises a material selected from graphene, transition metal dichalcogenide (TMD), or a combination thereof.

5. The apparatus of claim 1, wherein the dielectric substrate comprises a material selected from $Si_3N_4$, $Al_2O_3$, $SiO_2$, and $HfO_2$.

6. The apparatus of claim 1, wherein the dielectric substrate has a first surface and a second surface, and wherein each membrane of the plurality of membranes is positioned upon the first surface.

7. The apparatus of claim 1, wherein each pore has a diameter, and wherein the diameter of each pore is a same as the diameter of each other pore.

8. The apparatus of claim 1, wherein each pore has a diameter, and wherein at least one diameter has a different value from at least one other diameter.

9. The apparatus of claim 1, wherein each electrode pair comprises a respective source electrode and a respective drain electrode, and wherein each characteristic is a conductance associated with each respective pore.

10. The apparatus of claim 1, further comprising:
a processing system including a processor; and
a memory that stores executable instructions that, when executed by the processing system, facilitate performance of operations, the operations comprising:
simultaneously sensing via multi-channel measurements a first characteristic associated with a first one of the plurality of electrode pairs and a second characteristic associated with a second one of the plurality of electrode pairs.

11. The apparatus of claim 10, further comprising a dielectric cover, wherein each of the plurality of membranes is sandwiched between the dielectric substrate and the dielectric cover, and wherein each pore is associated with a second corresponding hole that extends through the dielectric cover.

12. The apparatus of claim 1, wherein each of the plurality of membranes is separated from each other of the plurality of membranes by a respective physical gap.

13. The apparatus of claim 1, wherein each electrode pair facilitates determination of a respective electrical characteristic.

14. The apparatus of claim 1, further comprising:
a processing system including a processor; and
a memory that stores executable instructions that, when executed by the processing system, facilitate performance of operations, the operations comprising:
simultaneously sensing via multi-channel measurements a characteristic associated with one of the plurality of electrode pairs and one or more other characteristics associated with each respective one of one or more other electrode pairs of the plurality of electrode pairs.

15. A method comprising:
sensing, by a processing system including a processor, a characteristic associated with a translocation of a biomolecule through a pore of a membrane of a plurality of membranes, wherein the membrane is disposed on a dielectric substrate, wherein the pore goes through the membrane, wherein the pore is associated with a corresponding hole that extends through the dielectric substrate, and wherein the membrane is in electrical contact with a pair of electrodes via which the characteristic is sensed; and
sensing, by the processing system, another characteristic associated with another translocation of another biomolecule through another pore of another membrane of the plurality of membranes, wherein the another membrane is disposed on the dielectric substrate, wherein the another pore goes through the another membrane, wherein the another pore is associated with a corresponding another hole that extends through the dielectric substrate, wherein a physical gap exists between the another membrane and the membrane such that the another membrane is not in direct contact with the membrane, wherein the another membrane is not in electrical contact with the pair of electrodes, and wherein the another membrane is in electrical contact with another pair of electrodes via which the another characteristic is sensed.

16. The method of claim 15, wherein:
each of the characteristic and the another characteristic is a respective electrical characteristic; and
each of the biomolecule and the another biomolecule comprises a respective DNA strand, a respective RNA strand, or a respective protein.

17. The method of claim 15, wherein the characteristic is sensed at essentially a same time that the another characteristic is sensed and wherein the plurality of membranes is disposed as an array.

18. The method of claim 15, wherein the pore has a diameter, wherein the another pore has another diameter, and wherein the diameter is a same as the another diameter.

19. The method of claim 15, wherein the pore has a diameter, wherein the another pore has another diameter, and wherein the diameter has a different value from the another diameter.

20. The method of claim 15, wherein:
each of the membrane and the another membrane comprises a respective semiconductor material;

each semiconductor material comprises a respective two-dimensional material;

each two-dimensional material comprises respective graphene, respective transition metal dichalcogenide (TMD), or a respective combination thereof; and the dielectric substrate comprises a material selected from $Si_3N_4$, $Al_2O_3$, $SiO_2$, and $HfO_2$.

21. A machine-readable storage medium comprising executable instructions that, when executed by a processing system including a processor, perform operations, the operations comprising:

obtaining a first electrical characteristic associated with a first translocation of a first biomolecule through a first pore of a first membrane of a plurality of membranes, wherein the first membrane is located on a dielectric substrate, wherein the first pore goes through the first membrane, wherein the first pore is associated with a corresponding first hole that extends through the dielectric substrate, and wherein the first membrane is in electrical contact with a first pair of electrodes via which the first electrical characteristic is sensed; and obtaining a second electrical characteristic associated with a second translocation of a second biomolecule through a second pore of a second membrane of the plurality of membranes, wherein the second membrane is located on the dielectric substrate, wherein the second pore goes through the second membrane, wherein the second pore is associated with a corresponding second hole that extends through the dielectric substrate, wherein a physical gap exists between the second membrane and the first membrane such that the second membrane is not in direct contact with the first membrane, wherein the second membrane is not in electrical contact with the first pair of electrodes, and wherein the second membrane is in electrical contact with a second pair of electrodes via which the second electrical characteristic is sensed.

22. The machine-readable storage medium of claim 21, wherein each of the first biomolecule and the second biomolecule comprises a respective DNA strand, a respective RNA strand, or a respective protein.

23. The machine-readable storage medium of claim 21, wherein the first electrical characteristic and the second electrical characteristic are sensed substantially simultaneously.

* * * * *